United States Patent
Yamaguchi et al.

(10) Patent No.: US 7,281,797 B2
(45) Date of Patent: Oct. 16, 2007

(54) OPTICAL-CHARACTERISTIC MEASUREMENT APPARATUS AND FUNDUS-IMAGE OBSERVATION APPARATUS

(75) Inventors: Tatsuo Yamaguchi, Tokyo (JP); Toshifumi Mihashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 299 days.

(21) Appl. No.: 11/155,903

(22) Filed: Jun. 20, 2005

(65) Prior Publication Data

US 2005/0286018 A1 Dec. 29, 2005

(30) Foreign Application Priority Data

Jun. 22, 2004 (JP) .............................. 2004-183389

(51) Int. Cl.
*A61B 3/10* (2006.01)
(52) U.S. Cl. ...................... 351/205; 351/206; 351/208; 351/209
(58) Field of Classification Search ................. 351/205, 351/206, 208–212
See application file for complete search history.

(56) References Cited

U.S. PATENT DOCUMENTS

| | | | |
|---|---|---|---|
| 5,777,719 A | 7/1998 | Williams et al. | |
| 6,299,307 B1 | 10/2001 | Oltean et al. | |
| 6,572,230 B2 * | 6/2003 | Levine | 351/221 |
| 6,736,507 B2 * | 5/2004 | Kudryashov et al. | 351/206 |
| 2003/0071969 A1 | 4/2003 | Levine et al. | |
| 2005/0286020 A1 * | 12/2005 | Campbell | 351/221 |

FOREIGN PATENT DOCUMENTS

| | | | |
|---|---|---|---|
| JP | 05-212002 A | | 8/1993 |
| JP | 09-094230 A | | 4/1997 |
| JP | 2002-209854 A | | 7/2002 |
| WO | WO 03/000153 A2 | | 1/2003 |
| WO | WO 03/020121 A1 | | 3/2003 |

* cited by examiner

*Primary Examiner*—Huy Mai
(74) *Attorney, Agent, or Firm*—Foley & Lardner LLP

(57) ABSTRACT

An eye-anterior-part observation system receives light reflected from an eye anterior part of the eye under measurement illuminated by an eye-anterior-part illumination light source. A movement-distance calculation section measures the displacement of the eye from an eye anterior image by the eye-anterior-part observation system. A wavefront compensation device compensates the wavefront of light reflected or transmitted. A wavefront-measurement section projects light on the eyeground, and receives light reflected from the eyeground through the wavefront compensation device. A calculation apparatus measures wavefront aberrations, based on the measured displacement of the eye and a light-receiving signal by the wavefront-measurement section. A wavefront-compensation-device control apparatus generates a control signal based on the wavefront aberration, and outputs to the wavefront compensation device to compensate the wavefront. A stage with a motor moves the wavefront compensation device in a direction transversing the optical axis of the reflected light, based on the displacement of the eye.

20 Claims, 18 Drawing Sheets

EXAMPLE FOR STRUCTURE OF MOVING ELEMENTS

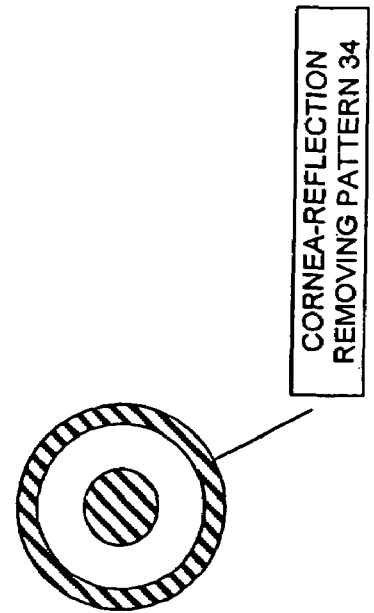
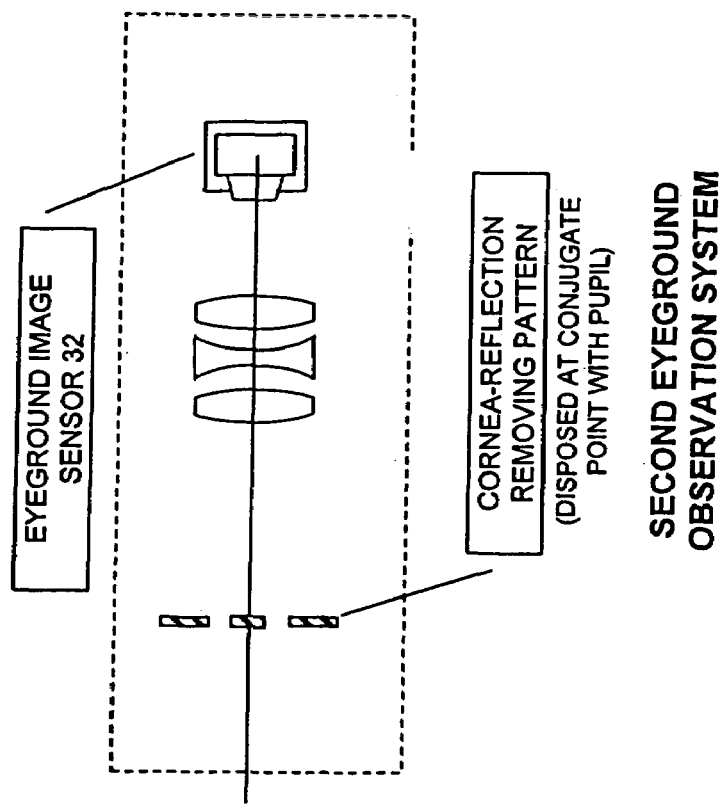

THIRD EYEGROUND OBSERVATION SYSTEM
(WHEN POLARIZATION DIRECTION OF LIGHT MODULATED BY WAVEFRONT COMPENSATION DEVICE IS P)

<PUPIL-MOVEMENT-DISTANCE CALCULATION>

<EDGE DETECTION>

APPLY LEAST SQUARE APPROXIMATION TO ELLIPTIC EQUATION
TO CALCULATE CENTER COORDINATES OF ELLIPSE

OBTAIN EYE-FRONT-PART IMAGE BY EYE-FRONT-PART
IMAGE SENSOR

EDGE DETECTION

<WAVEFRONT-COMPENSATION-DEVICE MOVEMENT>

<SHIFT-COMPUTATION WAVEFRONT MEASUREMENT>

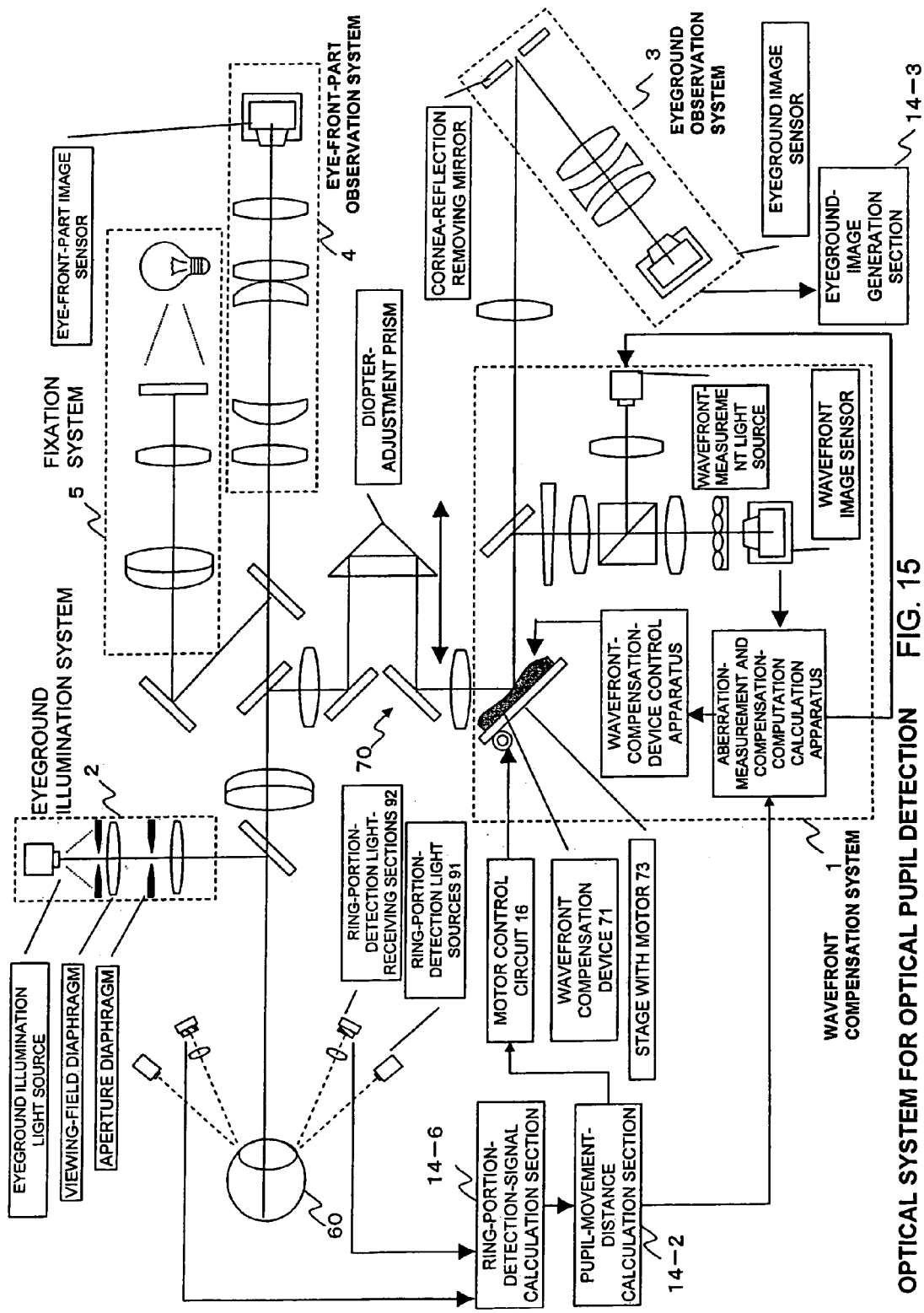
FIG. 15 OPTICAL SYSTEM FOR OPTICAL PUPIL DETECTION

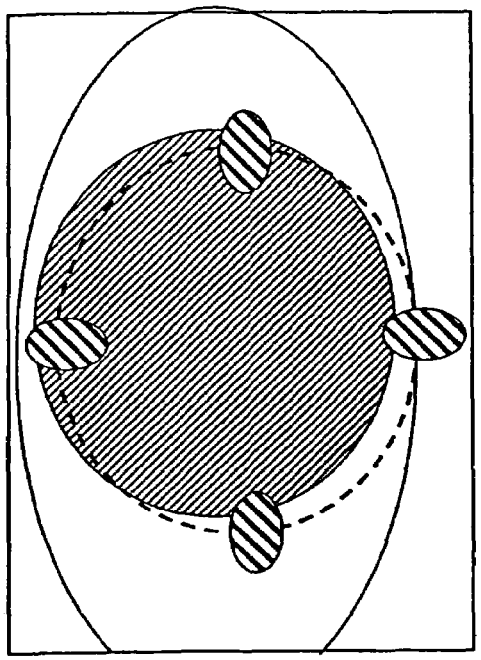

FIG. 16A

GENERATE m OPTICAL SYSTEMS FOR IRRADIATING LIGHT TO RING PORTION

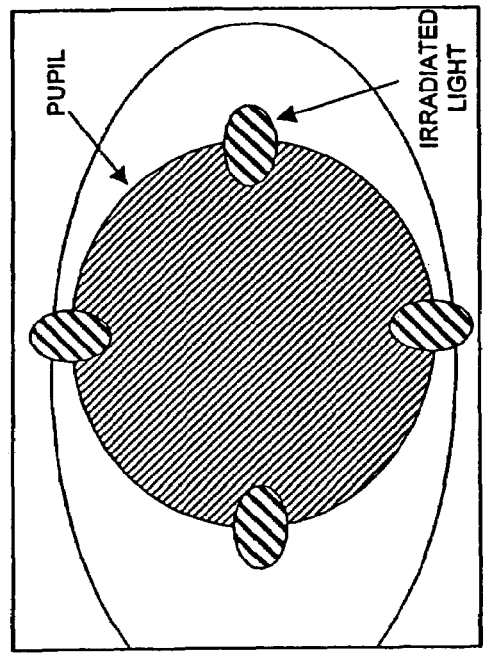

FIG. 16B

WHEN PUPIL MOVES, DETECTED QUANTITY OF LIGHT IS CHANGED AT RING-PORTION-DETECTION LIGHT-RECEIVING SECTIONS

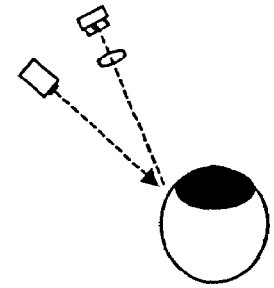

FIG. 16E

DETECTED QUANTITY OF LIGHT W > $W_1$ WHEN PUPIL MOVES AWAY FROM OPTICAL-AXIS DIRECTION

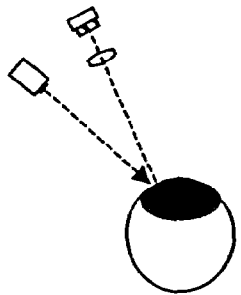

FIG. 16D

DETECTED QUANTITY OF LIGHT W < $W_1$ WHEN PUPIL MOVES TOWARD OPTICAL-AXIS DIRECTION

FIG. 16C

INITIAL DETECTED QUANTITY OF LIGHT $W_1$ AT NO SHIFT

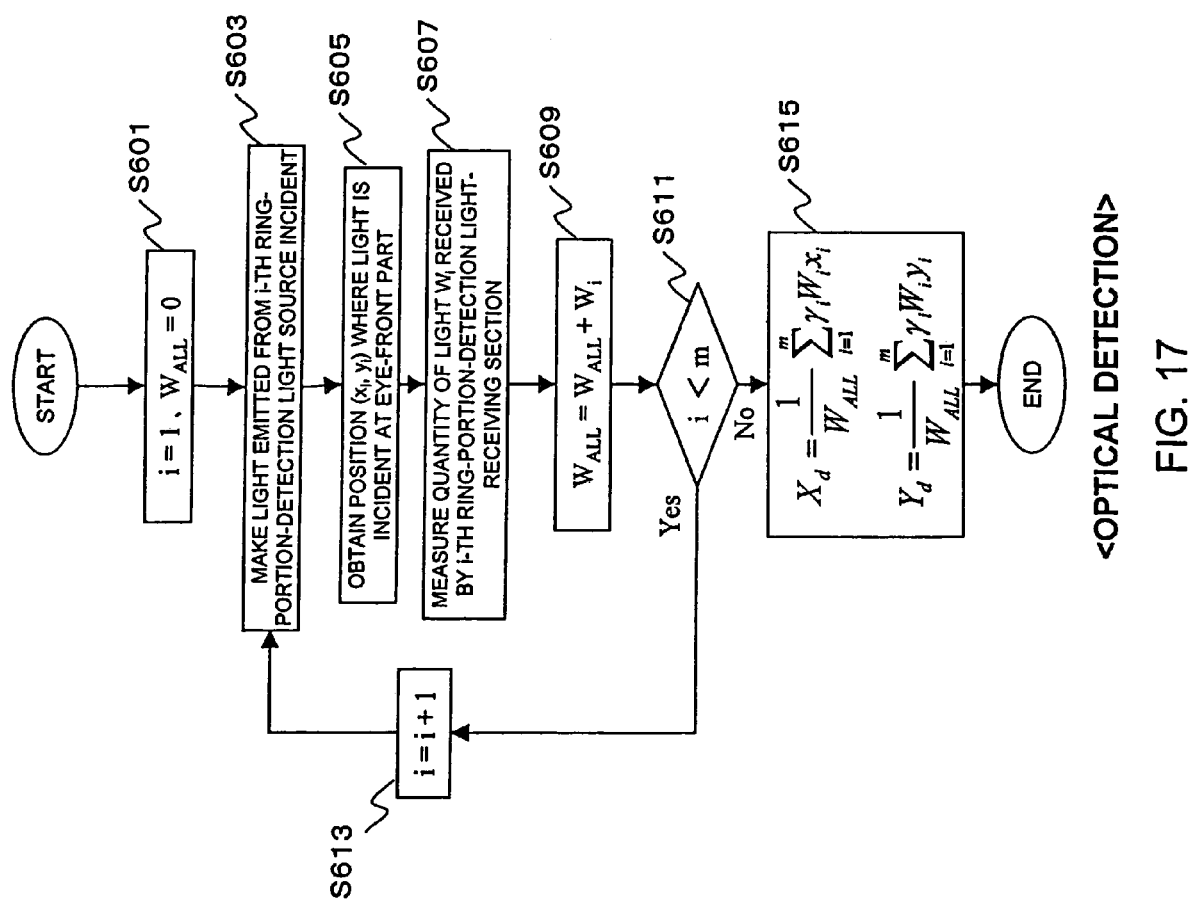
FIG. 17 <OPTICAL DETECTION>

OPTICAL-CHARACTERISTIC MEASUREMENT APPARATUS AND FUNDUS-IMAGE OBSERVATION APPARATUS

BACKGROUND OF THE INVENTION

1. Field of the Invention

The present invention relates to optical-characteristic measurement apparatuses and fundus-image observation apparatuses, and more particularly, to an optical-characteristic measurement apparatus and fundus-image observation apparatus for obtaining an optical characteristic and fundus-image of an eye under measurement, respectively, by compensating a wavefront by a wavefront compensation device.

2. Description of the Related Art

Recently, optical instruments used in the medical field have been spread. Especially in ophthalmology, optical-characteristic measurement apparatuses for checking eye functions such as the refraction and adjustment of eyes and the insides of eyeballs have been spread. For example, there exists a photorefractometer for obtaining the refractive degree and the corneal shape of an eye under measurement. In a conventional eyeground observation, an eyeground was observed with adjustment performed to reduce the effect of eye aberration as much as possible.

Apparatuses which allow an apparatus optical system to be aligned with an eye under measurement by observing an eye anterior part of the eye under measurement have also been disclosed, such as those disclosed in Japanese Unexamined Patent Application Publication No. Hei-5-212002 and No. Hei-9-94230. Japanese Unexamined Patent Application Publication No. Hei-5-212002 discloses that the positional coordinates in X and Y directions of a bright-point image reflected by a cornea are detected by an alignment detection sensor, and a motor is driven based on the positional information in the X and Y directions to move the entire apparatus. With this operation, the optical axis of an apparatus optical system is aligned with the optical axis of the eyeball of the eye under measurement.

Japanese Unexamined Patent Application Publication No. Hei-9-94230 discloses that a motor is driven based on a detection signal of an X-and-Y-direction-alignment detection sensor such that an alignment bright-point image approaches the center of an automatic-imaging-allowed area, to move the apparatus body in X and Y directions. This publication also discloses that a plurality of locations in an eye under measurement can be consecutively captured after alignment is performed once.

In adaptive optics, one of issues raised when a wavefront compensation device is used in order to compensate for aberrations of a human eye is the positional movement of the eye. The eye has been fixed as much as possible by, for example, asking the person to bite a "bite bar" used in dentistry. This method imposes a burden on the person, and does not fundamentally settle the issue of how to fix the position of the eye. Since the apparatus itself is moved in each of Japanese Unexamined Patent Application Publication No. Hei-5-212002 and No. Hei-9-94230, the apparatuses are not suited, for example, to a case where a high magnification is used.

SUMMARY OF THE INVENTION

Accordingly, it is an object of the present invention to provide an optical-characteristic measurement apparatus for measuring an optical characteristic and an fundus-image observation apparatus for forming an fundus-image by performing stable wavefront compensation even if an eye under measurement moves.

According to a first solving means of the present invention, there is provided, an optical-characteristic measurement apparatus comprising:

an eye-anterior-part illumination light source for illuminating an eye anterior part of an eye under measurement;

an eye-anterior-part observation section for receiving light reflected from the eye anterior part of the eye under measurement illuminated, and for generating an eye anterior image of the eye under measurement;

a movement-distance calculation section for measuring the displacement of the eye under measurement indicating the shift between an optical axis and the eye under measurement, based on the generated eye anterior image;

a wavefront compensation device for compensating the wavefront of light reflected or transmitted, based on a given control signal;

a wavefront measurement section for projecting light used for wavefront measurement on the eyeground of the eye under measurement and for receiving light reflected from the eyeground of the eye under measurement through the wavefront compensation device;

an aberration calculation section for measuring wavefront aberration of the eye under measurement, based on the displacement of the eye under measurement measured by the movement-distance calculation section and a light-receiving signal obtained by the wavefront measurement section;

a stage for moving the wavefront compensation device, based on the displacement of the eye under measurement measured by the movement-distance calculation section, in a direction transversing the optical axis of the light reflected from the eyeground of the eye under measurement or in a direction of a plane perpendicular to a normal line of the wavefront compensation device; and a wavefront-compensation-device control apparatus for generating a control signal used to perform wavefront compensation such that aberration becomes small, based on the wavefront aberration measured by the aberration calculation section, and for outputting the generated control signal to the wavefront compensation device to compensate the wavefront, wherein the aberration calculation section measures an optical characteristic of the eye under measurement, based on the compensation of the wavefront compensation device corresponding to the control signal for the wavefront compensation, the displacement of the eye under measurement measured by the movement-distance calculation section, and the light-receiving signal obtained by the wavefront measurement section after the wavefront is compensated by the wavefront compensation device.

According to a second solving means of the present invention, there is provided, an fundus-image observation apparatus comprising:

an eye-anterior-part illumination light source for illuminating an eye anterior part of an eye under measurement;

an eye-anterior-part observation section for receiving light reflected from the eye anterior part of the eye under measurement illuminated, and for generating an eye anterior image of the eye under measurement;

a movement-distance calculation section for measuring the displacement of the eye under measurement indicating the shift between an optical axis and the eye under measurement, based on the generated eye anterior image;

a wavefront compensation device for compensating the wavefront of light reflected or transmitted, based on a given control signal;

a wavefront measurement section for projecting light used for wavefront measurement on the eyeground of the eye under measurement and for receiving first light reflected from the eyeground of the eye under measurement illuminated by the light used for wavefront measurement, through the wavefront compensation device;

an aberration calculation section for measuring wavefront aberration of the eye under measurement, based on the displacement of the eye under measurement measured by the movement-distance calculation section and a light-receiving signal obtained by the wavefront measurement section;

an eyeground illumination system for illuminating a predetermined area on the eyeground of the eye under measurement with light for eyeground observation;

an eyeground observation system for receiving second light reflected from the eyeground of the eye under measurement illuminated by the light emitted by the eyeground illumination system, through the wavefront compensation device, and for generating an fundus-image;

an fundus-image generation section for obtaining the fundus-image generated by the eyeground observation system and for displaying or outputting the fundus-image;

a stage for moving the wavefront compensation device, based on the displacement of the eye under measurement measured by the movement-distance calculation section, in a direction transversing the optical axis of the first and/or second light reflected from the eyeground of the eye under measurement or in a direction of a plane perpendicular to a normal line of the wavefront compensation device; and a wavefront-compensation-device control apparatus for generating a control signal used to perform wavefront compensation such that aberration becomes small, based on the wavefront aberration measured by the aberration calculation section, and for outputting the generated control signal to the wavefront compensation device to compensate the wavefront, wherein the fundus-image generation section obtains an fundus-image which is after the stage is moved and compensated by the wavefront compensation device.

According to the present invention, an optical-characteristic measurement apparatus for measuring an optical characteristic and an fundus-image observation apparatus for forming an fundus-image both by performing stable wavefront compensation even if an eye under measurement moves, are provided.

The present invention can be used, for example, in industries related to apparatuses for measuring optical characteristics of eyes and fundus-images.

BRIEF DESCRIPTION OF THE DRAWINGS

FIG. 6A and FIG. 6B show a first modification of an eyeground observation system.

FIG. 15 is a view showing the structure of an eyeground observation apparatus for performing optical pupil detection.

FIG. 16A to FIG. 16E are views showing an outline of the optical pupil detection.

FIG. 17 is a flowchart of the optical pupil detection.

DESCRIPTION OF THE PREFERRED EMBODIMENTS

Figure 1:
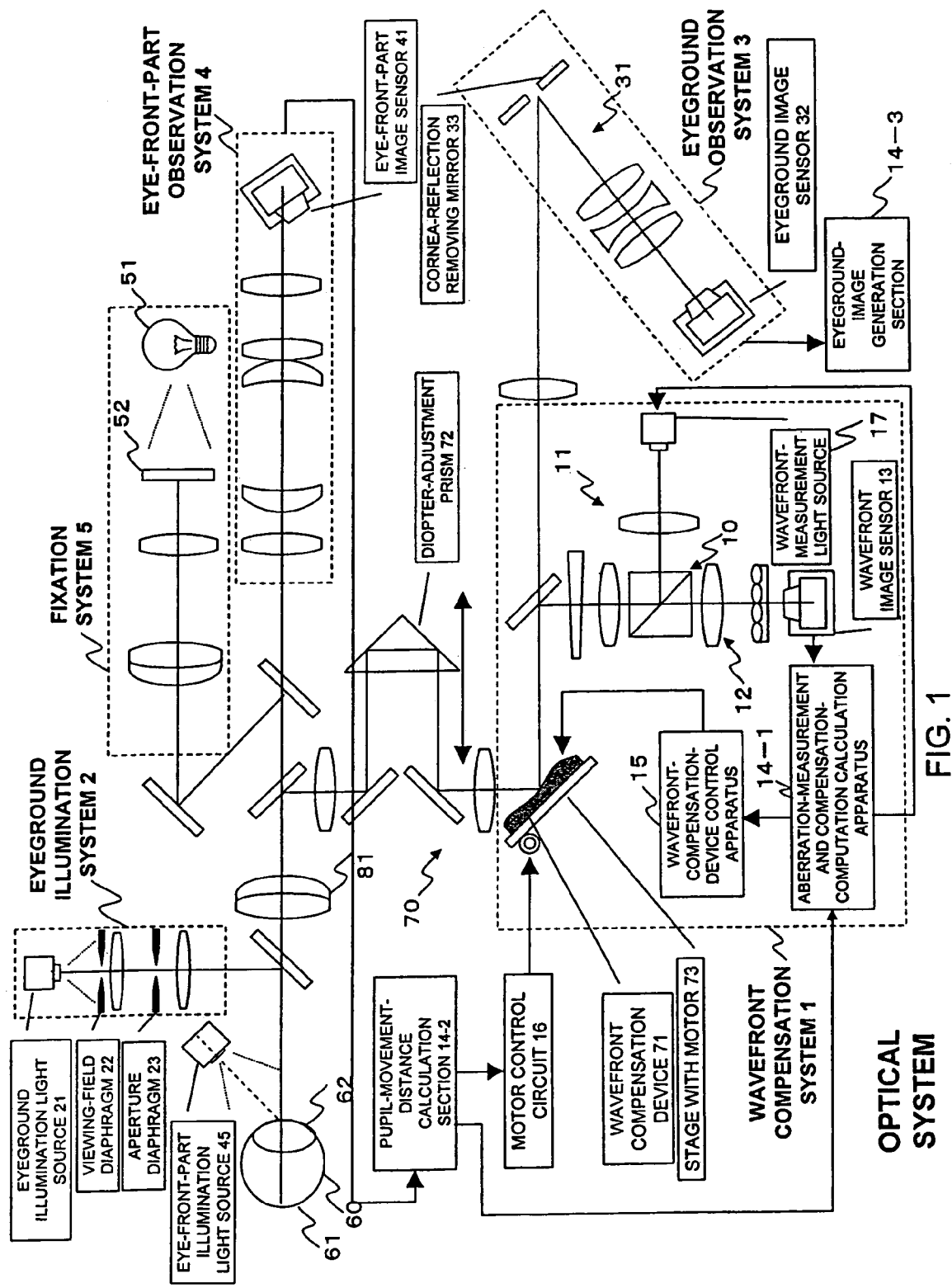
FIG. 1 is a view showing the structure of an eyeground observation apparatus according to an embodiment of the present invention.

Embodiments of the present invention will be described below by referring to the drawings.

1. Hardware Structure

FIG. 1 is a view showing the structure of an eyeground observation apparatus. The eyeground observation apparatus includes a wavefront compensation system 1, an eyeground illumination system 2, an eyeground observation system 3, an eye-anterior-part observation system 4, an eye-anterior-part illumination light source 45, a fixation system 5, a compensation optical section 70, a motor control circuit 16, a pupil-movement-distance calculation section 14-2, and an fundus-image generation section 14-3.

The wavefront compensation system 1 includes a first illumination optical system 11, a first light-receiving optical system 12, a wavefront measurement system 10 having a second light-receiving section 13, an aberration-measurement and compensation-computation calculation apparatus (aberration calculation section, hereinafter called a calculation apparatus) 14-1, and a wavefront-compensation-device control apparatus 15. The calculation section 14-1, the pupil-movement-distance calculation section 14-2, and the fundus-image generation section 14-3 can, for example, be provided for one computer 14 or a plurality of computers 14. In the figure, a retina (eyeground) 61 and a cornea (eye anterior part) 62 are shown in an eye under measurement 60.

The first illumination optical system (point-image projection optical system) 11 includes, for example, a first light source section (for example, a wavefront-measurement light source) 17, and illuminates a minute area (or a target) on the eyeground of the eye under measurement by a light beam emitted from the first light source section 17. The first illumination optical system 11 also includes, for example, a condenser lens and a relay lens.

It is preferred that the first light source section 17 have high spatial coherence and not-high temporal coherence. As an example, a super luminescence diode (SLD) is employed here as the first light source section 17, and serves as a point light source having high luminance. The first light source section 17 is not limited to an SLD, and may be a laser source, which has high spatial and temporal coherence, if the temporal coherence is appropriately reduced by inserting a rotary diffusing plate. The first light source section 17 may be an LED, which has not-high spatial and temporal coherence, if its quantity of light is sufficient and a pinhole is inserted on the optical path at the position of the light source. The first wavelength of the first light source section 17 used for illumination is, for example, a wavelength in an infrared region, such as 780 nm.

The first light-receiving optical system (point image light-receiving optical system) 12 receives light reflected by and returned from the retina and guides it to the first light-receiving section (such as a wavefront image sensor) 13. The first light-receiving optical system includes a relay lens, a beam splitter, and a conversion member (a splitting device such as a Hartman plate) for converting the reflected light beam into at least 17 beams. The beam splitter is formed of a mirror (such as a polarization beam splitter) which reflects light emitted from the first light source section 17 and transmits the reflected light beam reflected by the retina of the eye under measurement 60 and returned through an afocal lens 81. The conversion member is a wavefront conversion member for converting the reflected light beam into a plurality of beams. A plurality of micro Fresnel lenses disposed on a plane perpendicular to the optical axis can be used as the conversion member. The light beam reflected from the eyeground 61 is condensed on the first light-receiving section 13 through the conversion member.

The first light-receiving section 13 receives light from the first light-receiving optical system 12, which is transmitted through the conversion member, and generates a first signal. The front focus of the afocal lens 81 almost equals the pupil of the eye under measurement 60 in position.

While the first illumination optical system 11 and the first light-receiving optical system 12 keep a relationship such that, assuming that light emitted from the first light source section 17 is reflected at a point where the light is condensed, the first light-receiving section 13 has the maximum signal peak of the reflected light, a prism 72 can be moved in a direction in which the signal peak obtained by the first light-receiving section 13 increases and stopped at a position where the signal peak reaches the maximum. As a result, the light emitted from the first light-source section 17 is condensed on the eye under measurement.

The second illumination optical system (eyeground illumination system) 2 includes, for example, a second light source section 21, a viewing-field diaphragm 22, an aperture diaphragm 23, a condenser lens, and a beam splitter, and illuminates a predetermined area on the retina (eyeground) of the eye under measurement by a second light beam emitted from the second light source section 21. The second light source section 21 emits, for example, a red light beam having a second wavelength of 630 nm, and serves as a point light source or a surface light source for the eyeground 61 to generate a red area. The first light source section 17 used for Hartman measurement can have an appropriate wavelength such as a wavelength of 840 nm, and the eye-anterior-part illumination light source 45 can have an appropriate wavelength such as a wavelength ranging from 850 nm to 930 nm (in the current case, from 860 nm to 880 nm) in an infrared or near-infrared region. The beam splitter can, for example, be a beam splitter which reflects light emitted from the second light source section 21 and transmits a light beam reflected by and returned from the eye under measurement 60.

As shown in FIG. 1, light is incident from the inside of the pupil and a plate (such as a mirror with an opening used in the figure) which blocks light is inserted at a conjugate point with the cornea and the crystalline lens, so that noise (uninvited reflection) caused by the cornea and others can be removed. The aperture diaphragm 23 of the eyeground illumination system 2 can be disposed close to a conjugate point with the pupil to make an optical system which removes noise light by a cornea-reflection removing mirror, described later. The viewing-field diaphragm 22 is disposed at a conjugate point with the eyeground. With this, light can be concentrated on an area where a cell is observed, and a load imposed on the person under measurement can be reduced.

When a mirror with an opening is used, the mirror with the opening and the pupil are made to have a conjugate relationship in order to prevent reflection at a vertex of the cornea. A ring-shaped aperture may also be used when the center thereof has a transmittance of 100%, surroundings of the center have a transmittance of about 10%, and light transmitting the surroundings illuminates the whole of the eyeground 61.

The eyeground observation system 3 includes a second light-receiving optical system 31 and a second light-receiving section (such as an fundus-image sensor) 32. The second light-receiving optical system (fundus-image-generation optical system) 31 includes, for example, the afocal lens 81, a beam splitter, a condenser lens, and a cornea-reflection removing mirror 33, and guides light having a second wavelength reflected from the eyeground 61 to the second light-receiving section 32 through the compensation optical section 70. The beam splitter is formed, for example, of a dichroic mirror which reflects light having the first wavelength and transmits light having the second wavelength. The second light-receiving section 32 receives an fundus-image generated by the second light-receiving optical system 31 and generates a second signal. The second light-receiving section 32 can be formed of a light-receiving device sensitive to the second wavelength (red light).

The cornea-reflection removing mirror 33 is preferably used at a small angle in order to make the pupil conjugate. Using an optical system like a second eyeground observation system, described later, is an effective way. In the present embodiment, the afocal lens 81, the beam splitter, and others are provided for the second light-receiving optical system 31 for convenience. They may be provided for the first light-receiving optical system 12.

The compensation optical section 70 has a wavefront compensation device 71 such as adaptive optical system (adaptive optics) for compensating measurement light for aberration, the moving prism 72 for moving along the optical axis to compensate a spherical component and/or a spherical lens, and a stage 73 with a motor. The compensation optical section 70 is disposed in the first and second light-receiving optical systems 12 and 31, and compensates, for example, for the aberration of a reflected light beam reflected by and returned from the eye under measurement 60. The compensation optical section 70 may compensate light emitted from the first light source 17 for aberration to illuminate a minute area on the eyeground of the eye under measurement by a light beam of which aberration has been compensated for.

The wavefront compensation device 71 can be a variable-shape mirror (a deformable mirror or a variable mirror) or a spatial light modulator such as liquid crystal. An appropriate optical system capable of compensating measurement light for aberration may also be used. A variable-shape mirror changes the reflection direction of light by deforming the mirror by an actuator provided inside the mirror. Other appropriate deforming methods can be used such as a deforming method using a capacitor or a piezoelectric device. A liquid-crystal spatial light modulator uses a liquid-crystal alignment characteristic to modulate a phase, and is used in reflection in many cases in the same way as the variable-shape mirror. When the liquid-crystal spatial light modulator is used, a polarizer is required in an optical path in some cases. The wavefront compensation device 71 may be a transmission-type optical system, in addition to a reflection-type optical system. The wavefront compensation device 71 compensates for aberration by, for example, being deformed according to the output of the wavefront-compensation-device control apparatus 15.

It is preferred that a parallel light beam be incident on the wavefront compensation device 71. Incident light is not limited to parallel light beams. When the eye under measurement 60 has no aberration, for example, light reflected from the retina of the eye under measurement 60 is incident on the wavefront compensation device 71 as a parallel light beam. Light emitted from the first light source section 17 is incident on the wavefront compensation device 71 as a parallel light beam.

The moving prism 72 is moved according to the output of the computer 14. The moving prism 72 is driven, for example, by an appropriate driving section. A spherical component can be compensated for because the moving prism 72 is moved. The spherical component can be compensated for if a spherical lens is used, instead of moving the moving prism 72.

The stage 73 with a motor moves the wavefront compensation device 71 according to the output of the motor control circuit 16 by following the movement of the pupil. With this, one point (such as the center) of the wavefront compensation device 71 is always conjugate with one point (such as the center) of the pupil to implement stable wavefront compensation.

The eye-anterior-part illumination light source 45 illuminates an eye anterior part of the eye under measurement 60. For example, a Placido's ring or a keratoring may be used to project a predetermined pattern on the eye anterior part. When a keratoring is used, a pattern just around the center of curvature of the cornea is obtained by a keratoimage. The wavelength of light emitted from the eye-anterior-part illumination light source 45 is, for example, different from the first wavelength (780 nm in this case), and can be a long wavelength (such as 940 nm).

The eye-anterior-part observation system 4 includes a condenser lens and an eye-anterior-part image sensor 41, and guides a light beam emitted from the eye-anterior-part illumination light source 45 and reflected by and returned from the cornea 62 of the eye under measurement 60, to the eye-anterior-part image sensor 41. As a light source section, an appropriate light source for illuminating the eye under measurement 60 may be used instead of the eye-anterior-part illumination light source 45. The eye-anterior-part observation system 4 can also guide a light beam reflected by and returned from the eye anterior part or the cornea 62 of the eye under measurement 60 when an appropriate pattern (such as a Placido's ring) is projected on the eye under measurement 60, to the eye-anterior-part image sensor 41. The eye-anterior-part image sensor 41 can obtain an eye-anterior-part image. The eye-anterior-part observation system 4 can also be used for alignment. The wavelength of light used for alignment can be a long wavelength (such as 940 nm) different, for example, from the first wavelength (780 nm in this case).

The third illumination optical system (fixation system) 5 includes, for example, an optical path for projecting an eyesight-target for making the eye under measurement 60 have fixation or clouding and fogging, and is provided with a third light source section (such as a lamp) 51, a fixation target 52, and a relay lens. The system 5 can project the fixation target 52 on the eyeground 61 with a light beam emitted from the third light source section 51, and makes the eye under measurement 60 observe its image.

The wavefront-compensation-device control apparatus 15 deforms the wavefront compensation device 71 according to the output of the computer 14. For example, the wavefront-compensation-device control apparatus 15 generates a control signal (such as a voltage) for deforming each element of the wavefront compensation device 71, based on wavefront aberration measured by the calculation apparatus 14-1 or based on compensation obtained by the calculation apparatus 14-1, and outputs the generated control signal to the wavefront compensation device 71 to compensate the wavefront. The wavefront-compensation-device control apparatus 15 also moves the moving prism 72 along the optical axis, based on the output of the computer 14. A spherical component can be compensated when the moving prism 72 is moved.

The motor control circuit 16 drives the motor of the stage 73 with the motor according to the displacement of the eye under measurement measured by the pupil-movement-distance calculation section 14-2 to move the stage 73 with the motor and the wavefront compensation device 71 in a direction transversing the optical axis or in a direction of a plane perpendicular to a normal line.

The calculation apparatus 14-1 obtains an optical characteristic which includes high-order aberrations of the eye under measurement 60, based on the output of the first light-receiving section 13. The calculation apparatus 14-1 may receive at least wavefront measurement data indicating the wavefront aberration of the eye under measurement 60 to obtain the optical characteristic, instead of receiving the output of the first light-receiving section 13. The calculation apparatus 14-1 determines the compensation of the wavefront compensation device according to the obtained optical characteristic, and outputs the compensation to the wavefront-compensation-device control apparatus 15.

The pupil-movement-distance calculation section 14-2 measures the displacement of the eye under measurement (such as the movement distance of the pupil) from the eye-anterior-part image generated by the eye-anterior-part image sensor 41. The pupil-movement-distance calculation section 14-2 can measure the movement distance of the center of the pupil as the displacement of the eye under measurement, but it may also obtain the movement distance of an appropriate position of the eye under measurement, such as the vertex of the cornea. The fundus-image generation section 14-3 obtains an fundus-image generated by the second light-receiving section 32, and displays or outputs the fundus-image.

Figure 2:
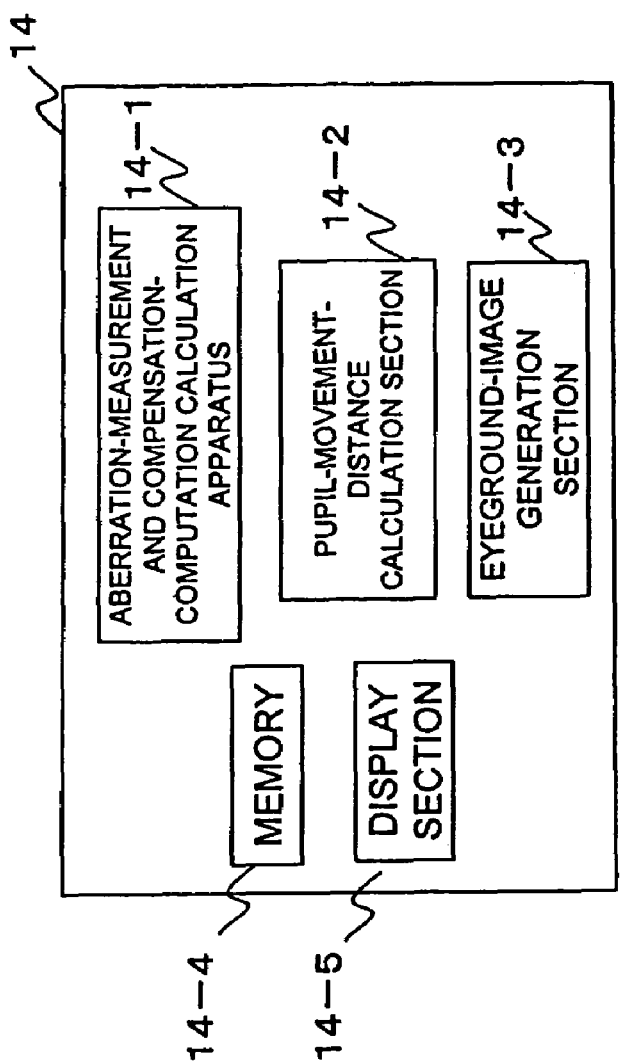
FIG. 2 is a view showing an example structure of a computer.

FIG. 2 shows an example structure of the computer 14. The calculation section 14-1, the pupil-movement-distance calculation section 14-2, and the fundus-image generation section 14-3 can, for example, be provided for one computer 14 or a plurality of computers 14. The computer 14 further includes a memory 14-4 and a display section 14-5. The computer 14 controls the entire apparatus.

The memory 14-4 stores, for example, the generated fundus-image, and also stores appropriate parameters determined in advance, obtained optical characteristics, and others. The display section 14-5 displays, for example, the generated fundus-image.

Conjugate Relationship

The eyeground 61 of the eye under measurement 60, the fixation target 52 in the fixation system 5, the first light source section 17, and the first light-receiving section 13 are conjugate. The pupil (iris) of the eye under measurement 60 and the conversion member (Hartman plate) of the first light-receiving optical system 12 are conjugate. The second light source section 21 is conjugate with the pupil (an image is formed on the pupil), and can uniformly illuminate the whole of most of the eyeground 61.

Alignment Adjustment

Alignment adjustment will be described next. For example, the eye-anterior-part observation system 4 can implement alignment adjustment.

Light emitted from the light source section illuminates the eye under measurement 60 through the condenser lens, the beam splitter, and the afocal lens 81, as a parallel light beam. A reflected light beam is reflected by the cornea 62 of the eye under measurement 60 as a divergent bundle of beams as if they were emitted from a point located at half the radius of curvature of the cornea 62. This divergent bundle of beams is received by the eye-anterior-part image sensor 41 as a spot image through the afocal lens 81, the beam splitter, and the condenser lens.

If the spot image is out of the optical axis on the eye-anterior-part image sensor 41, the entire eyeground observation apparatus is moved up and down and right and left to place the spot image in the optical axis. When the spot image is disposed in the optical axis, alignment adjustment is completed. Since an image of the eye under measurement 60 caused by a light source section, not shown, for illuminating the cornea 62 of the eye under measurement 60 is formed on the eye-anterior-part image sensor 41, the center of the pupil may be disposed in the optical axis by using this image in alignment adjustment.

Wavefront Compensation Device 71

Figure 3:
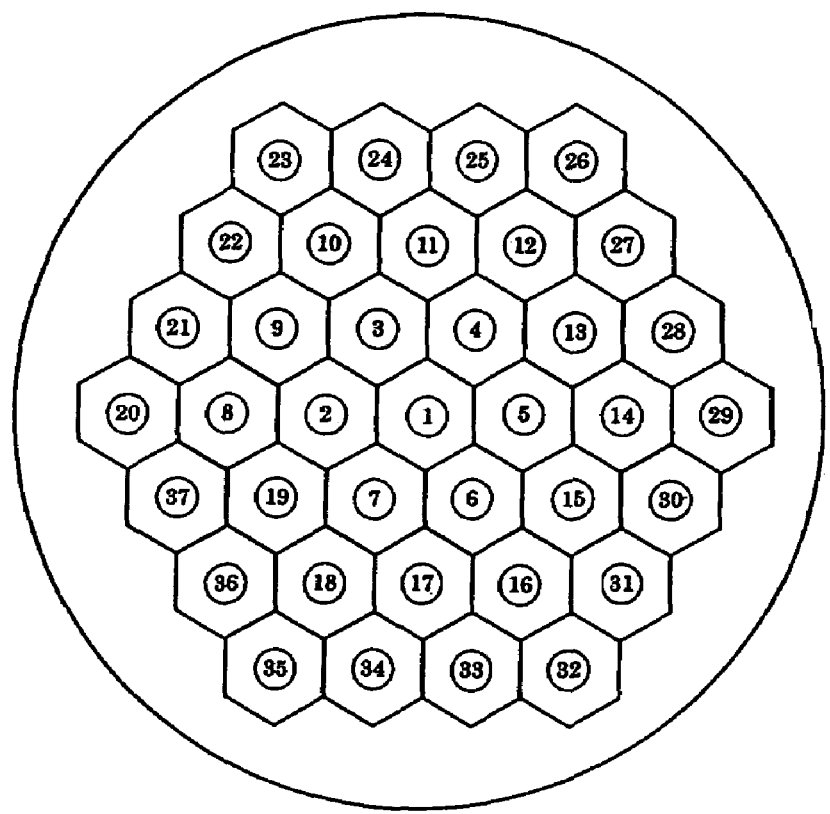
FIG. 3 is a view showing the structure of a wavefront compensation device.

FIG. 3 is a view showing the structure of the wavefront compensation device 71. When a variable-shape mirror is used, for example, each of a plurality of elements arranged in the mirror is moved by an actuator to deform the mirror. An element number to identify each element is assigned to the element in advance. The wavefront-compensation-device control apparatus 15 obtains, for example, the deformation (or the voltage) of each element corresponding to the compensation output from the calculation apparatus 14-1, and drives each element by a corresponding actuator. The number of elements is not limited to the number of elements shown in the figure. An appropriate number of elements can be used. An element number can be appropriately assigned to each element in a way different from the way shown in the figure. Instead of the element numbers, appropriate identification information which can identify each element, such as letters and coordinates can be used.

Figures 4A, 4B:
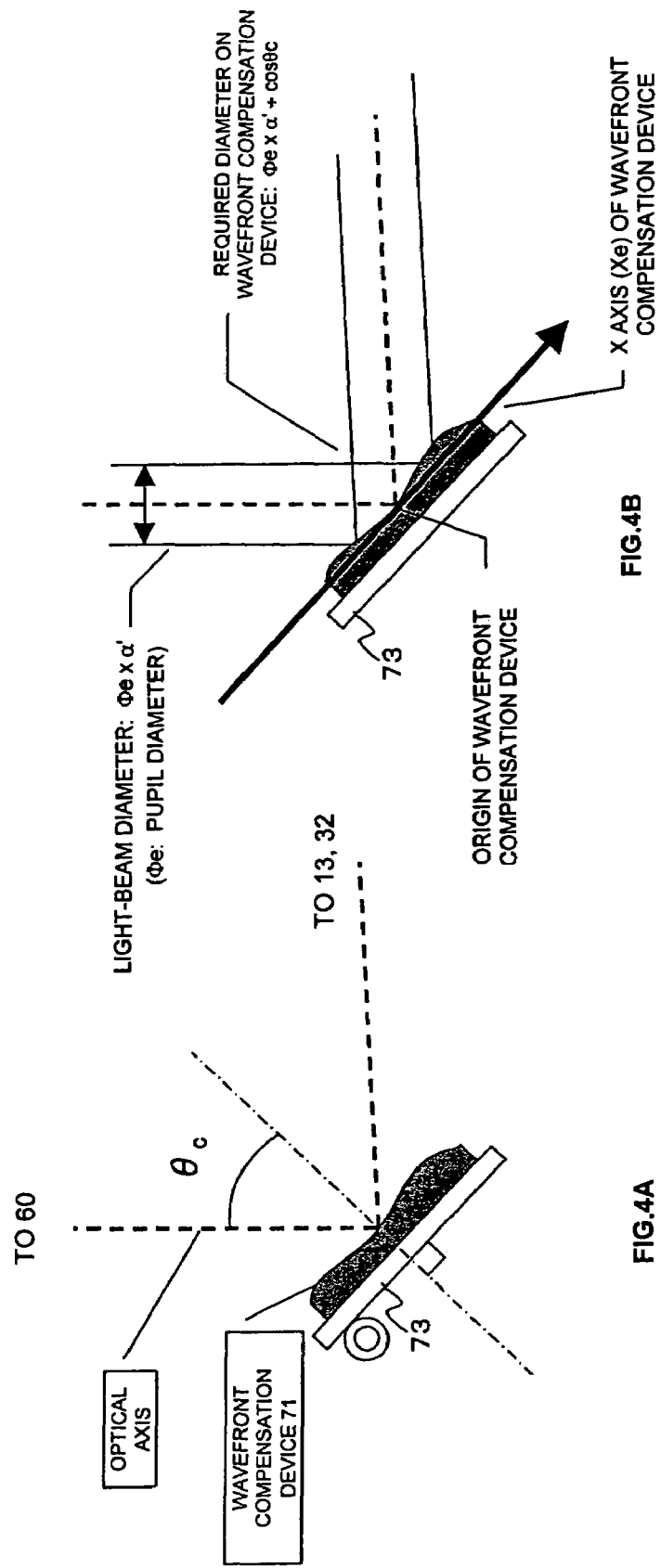
FIG. 4A and FIG. 4B are views of the wavefront compensation device.

FIG. 4A and FIG. 4B are views showing the wavefront compensation device 71. When the wavefront compensation device 71 is of a reflection type, the device is disposed such that the normal-line direction of the device 71 is at a predetermined angle $\theta c$ with respect to the optical axis, as shown in FIG. 4A. Assuming that the diameter of a light beam incident on the wavefront compensation device 71 is the pupil diameter $\Phi e$ multiplied by $\alpha'$, the required diameter in the tilted direction (the X direction Xe) of the device 71 is obtained by $\Phi e \times \alpha' \div \cos \theta c$, as shown in FIG. 4B, where $\alpha'$ is a magnification between the pupil and the wavefront compensation device 71 and can be set to a value determined in advance. When the pupil moves, the movement distance in the X-axis direction of the device 71 is set to a value corresponding to the movement distance of the pupil with the tilted angle of the wavefront compensation device 71 being taken into account.

Figure 5:
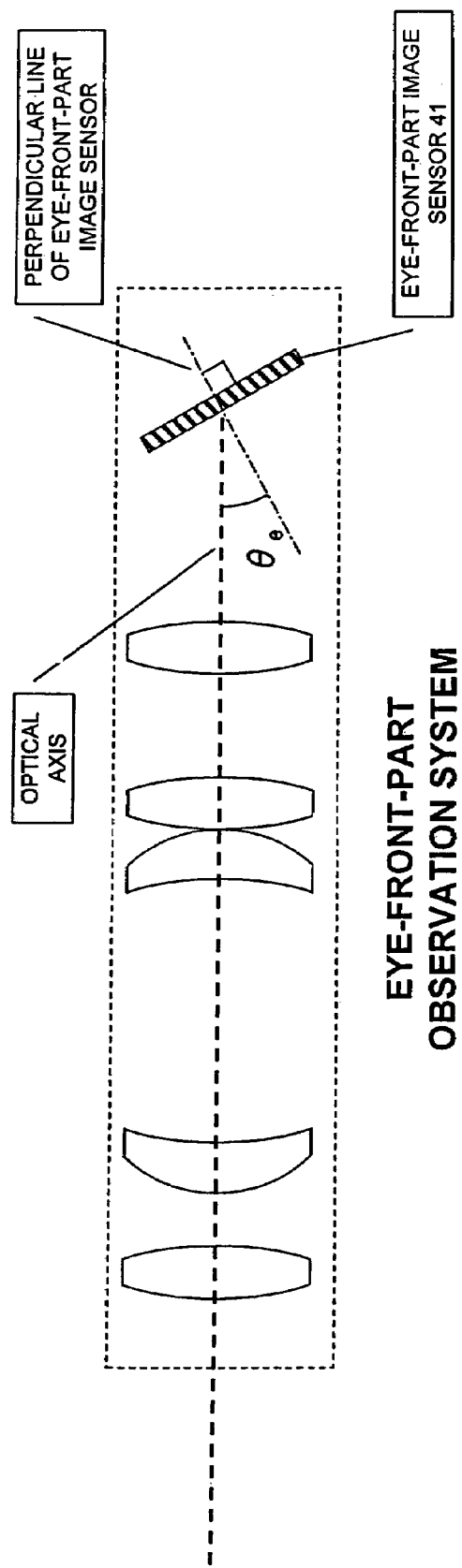
FIG. 5 is a view showing an eye-anterior-part image sensor.

FIG. 5 is a view showing the eye-anterior-part image sensor 41. The sensor 41 can be disposed such that the normal-line direction of the sensor 41 is at a predetermined angle $\theta e$ with respect to the optical axis. When the angle $\theta e$ between the perpendicular line of the sensor 41 and the optical axis is made equal, or almost equal to the angle $\theta c$ between the perpendicular line of the wavefront compensation device 71 and the optical axis, the amount of computation is reduced, and feedback speed is improved.

Modifications of the Eyeground Observation System

FIG. 6A and FIG. 6B show a first modification (a second eyeground observation system) of the eyeground observation system 3. The eyeground observation system 3 of the eyeground observation apparatus shown in FIG. 1 can be replaced with a second eyeground optical system 3-2 shown in FIG. 6A. The second eyeground optical system 3-2 includes an fundus-image sensor 32 and a cornea-reflection removing pattern 34. FIG. 6A shows only a portion corresponding to the eyeground observation system 3 enclosed by a dotted line in FIG. 1, but the configuration of the other portions is the same as in FIG. 1.

In the second eyeground observation system 3-2, the cornea-reflection removing pattern 34 is inserted at a position which makes the pupil and the cornea-reflection removing pattern 34 conjugate, to remove noise from the cornea to improve image quality. FIG. 6B shows an example structure of the cornea-reflection removing pattern 34. Whereas the eyeground observation system 3 shown in FIG. 1 is of a reflection type, since the second eyeground optical system 3-2 is of a transmission type, the optical path can be made straight.

Figure 7:
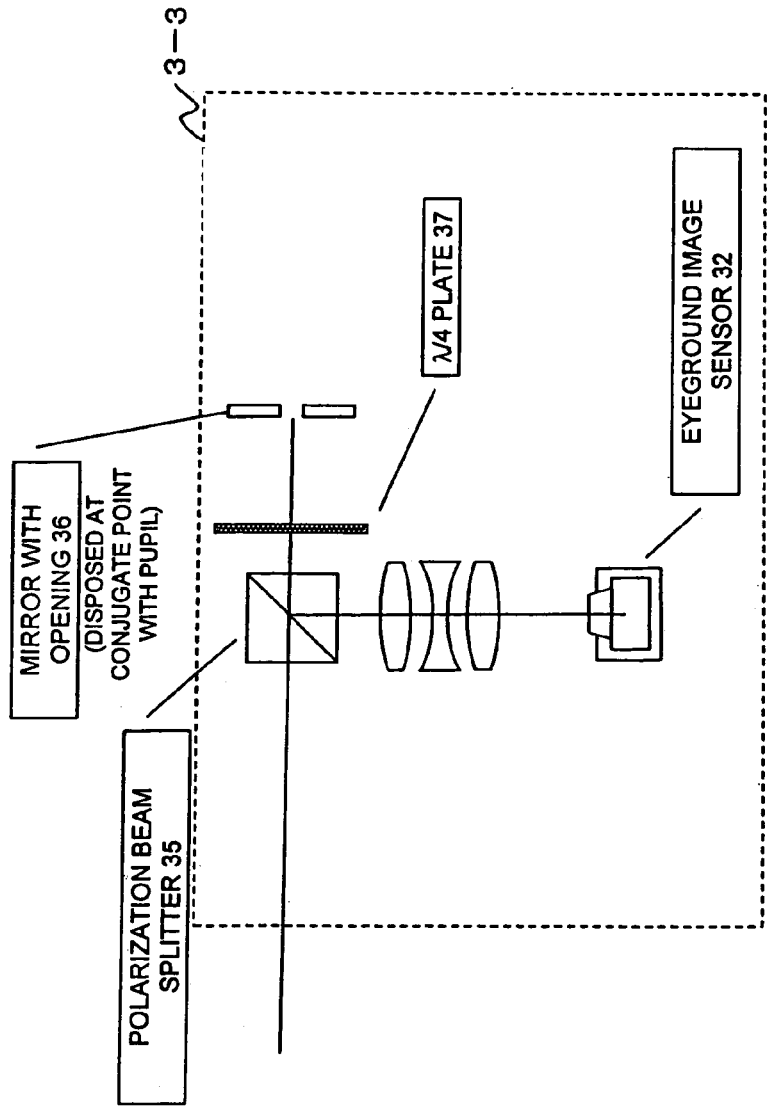
FIG. 7 shows a second modification of the eyeground observation system.

FIG. 7 shows a second modification (a third eyeground observation system) of the eyeground observation system 3. The eyeground observation system 3 of the eyeground observation apparatus shown in FIG. 1 can be replaced with a third eyeground optical system 3-3 shown in FIG. 7. When illumination light has a polarization characteristic, if the arrangement of the third eyeground observation system 3-3 is used, only noise is removed with the quantity of light being lost as little as possible. FIG. 7 shows a case in which the direction of polarization of light to which the wavefront compensation device applies modulation is P, which means that the polarization direction of the light is parallel to the plane of incidence.

The third eyeground optical system 3-3 includes a polarization beam splitter 35, a mirror 36 with an opening, and a $\lambda/4$ plate (wavelength plate) 37, where $\lambda$ indicates the wavelength. FIG. 7 shows only a portion corresponding to the eyeground observation system 3 enclosed by the dotted line in FIG. 1, but the configuration of the other portions is the same as in FIG. 1.

In the third eyeground observation system 3-3, the mirror 36 with the opening is disposed at a conjugate point with the pupil to remove noise from the cornea. Whereas the mirror 33 with the opening is disposed at an angle with respect to the optical axis in the eyeground observation system 3 shown in FIG. 1, since the mirror 36 with the opening is disposed perpendicular to the optical axis in the third eyeground optical system 3-3 shown in FIG. 7, noise light can be removed almost ideally.

The polarization beam splitter 35 transmits a light beam coming from the eye under measurement and modulated by the wavefront compensation device 71, to the λ/4 plate 37 and to the mirror 36 with the opening, and also reflects a light beam polarized by the λ/4 plate 37 and reflected from the mirror 36 with the opening, to the fundus-image sensor 32. Using the polarization beam splitter 35 removes uninvited light which is not compensated.

2. Zernike Analysis

Next, a Zernike analysis will be described. A generally known method of calculating Zernike coefficients $C_i^{2j-i}$ from Zernike polynomials will be described. The Zernike coefficients $C_i^{2j-i}$ are important parameters for grasping the optical characteristic of the subject eye 60 on the basis of inclination angles of the light fluxes obtained by the first light receiving part 23 through a modification member, for example the Hartmann plate 22.

Wavefront aberrations W(X, Y) of the subject eye 60 are expressed using the Zernike coefficients $C_i^{2j-i}$ and the Zernike polynomials $Z_i^{2j-i}$ by the following expression.

$$W(X, Y) = \sum_{i=0}^{n} \sum_{j=0}^{i} c_i^{2j-i} Z_i^{2j-i}(X, Y)$$

Where, (X, Y) denotes vertical and horizontal coordinates of the Hartmann plate 22.

Besides, with respect to the wavefront aberrations W(X, Y), when the horizontal and vertical coordinates of the first light receiving part 23 are denoted by (x, y), a distance between the Hartmann plate 22 and the first light receiving part 23 is denoted by f, and a movement distance of a point image received by the first light receiving part 23 is denoted by (Δx, Δy), the following expression is established.

$$\frac{\partial W(X, Y)}{\partial X} = \frac{\Delta x}{f}$$

$$\frac{\partial W(X, Y)}{\partial Y} = \frac{\Delta y}{f}$$

Where, the Zernike polynomials $Z_i^{2j-i}$ are expressed by the following numerical expressions. More specifically, for example, refer Japanese Unexamined Patent Application Publication No. 2002-209854.

$$Z_n^m = R_n^m(r) \left\{ \genfrac{}{}{0pt}{}{\sin}{\cos} \right\} \{m\theta\}$$

$m > 0$ sin $m \leq 0$ cos $$R_n^m(r) = \sum_{S=0}^{(n-m)/2} (-1)^S \frac{(n-S)!}{S! \left\{ \frac{1}{2}(n-m) - S \right\}! \left\{ \frac{1}{2}(n+m) - S \right\}!} r^m$$

Incidentally, with respect to the Zernike coefficients $C_i^{2j-i}$, specific values can be obtained by minimizing the squared error expressed by the following numerical expression.

$$S(x) = \sum_{i=1}^{data\ number} \left[ \left\{ \frac{\partial W(X_i, Y_i)}{\partial X} = \frac{\Delta x_i}{f} \right\}^2 + \left\{ \frac{\partial W(X_i, Y_i)}{\partial Y} = \frac{\Delta y_i}{f} \right\}^2 \right]$$

Where, W(X, Y): wavefront aberrations, (X, Y): Hartmann plate coordinates, (Δx, Δy): a movement distance of a point image received by the first light receiving part 23, f: a distance between the Hartmann plate 22 and the first light receiving part 23, m: the number of data.

The computer 14 calculates the Zernike coefficients $c_i^{2j-i}$, and uses them to obtain eye optical characteristics, such as spherical aberration, coma aberration, and astigmatism. The computer 14 also uses the Zernike coefficients $c_i^{2j-i}$ to calculate the quantity of aberration $RMS_i^{2j-i}$ by the following expression.

$$RMS_i^{2j-i} = \sqrt{\frac{\varepsilon_i^{2j-i}}{2(i+1)}} c_i^{2j-i}$$

$$\left( \varepsilon_i^{2j-i} = 2(2j=i), \varepsilon_i^{2j-i} = 1(2j \neq i) \right)$$

3. Flowchart

In the present embodiment, the center of the wavefront compensation device 71 follows the movement of the eye, and the compensation and the movement of the wavefront compensation device 71 are determined based on the output signal of the wavefront image sensor 13. For example, the wavefront compensation device 71 is disposed at a conjugate position with the pupil, and is moved in a direction transversing the optical axis (or a direction of a plane perpendicular to the normal line of the wavefront compensation device 71) by following the movement of the pupil. With this, a predetermined point on the wavefront compensation device 71 is always conjugate with a predetermined point on the pupil, implementing stable wavefront compensation.

Figure 8:
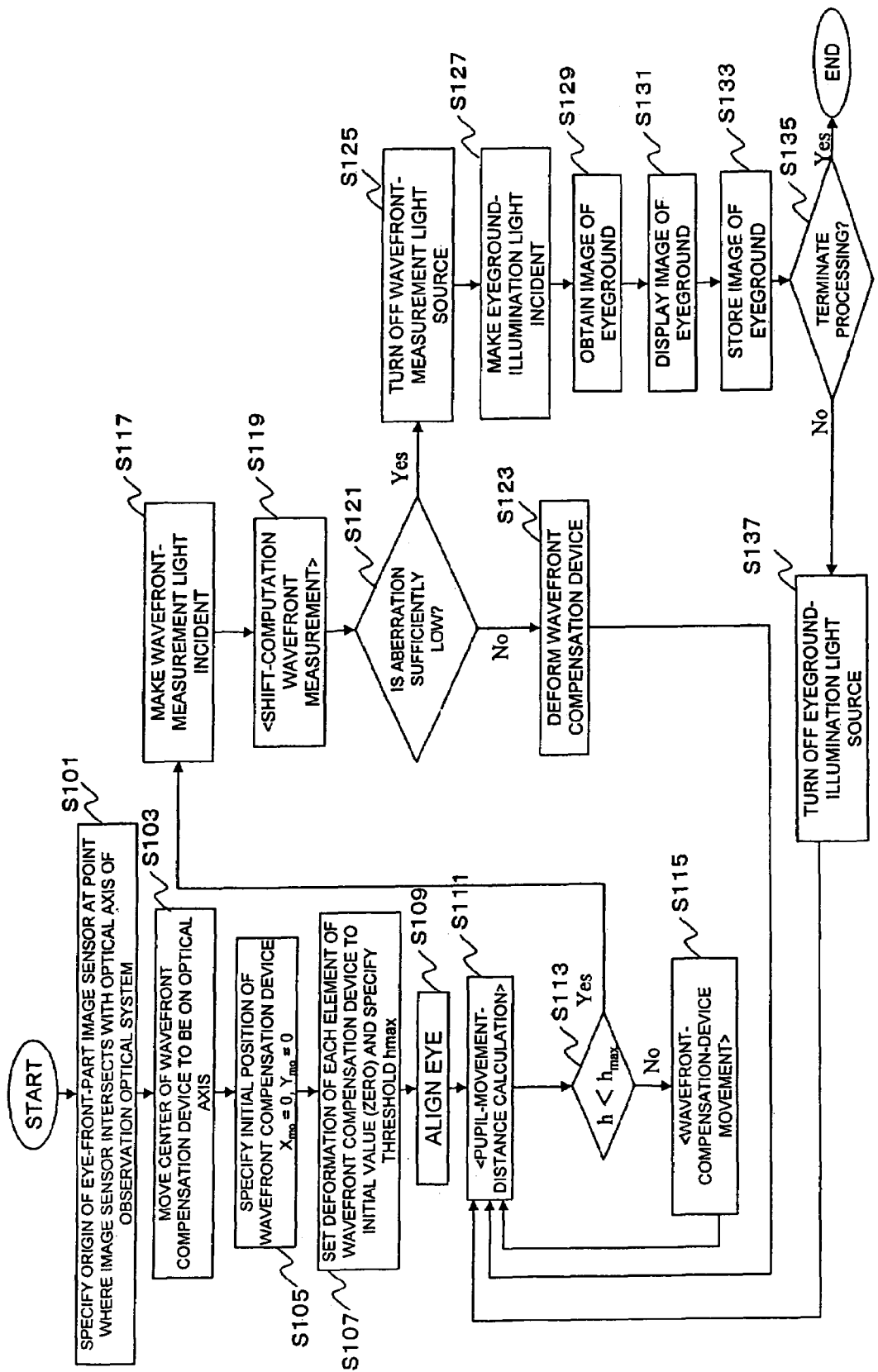
FIG. 8 is a flowchart of compensation-device movement adaptive optics.
Figure 9:
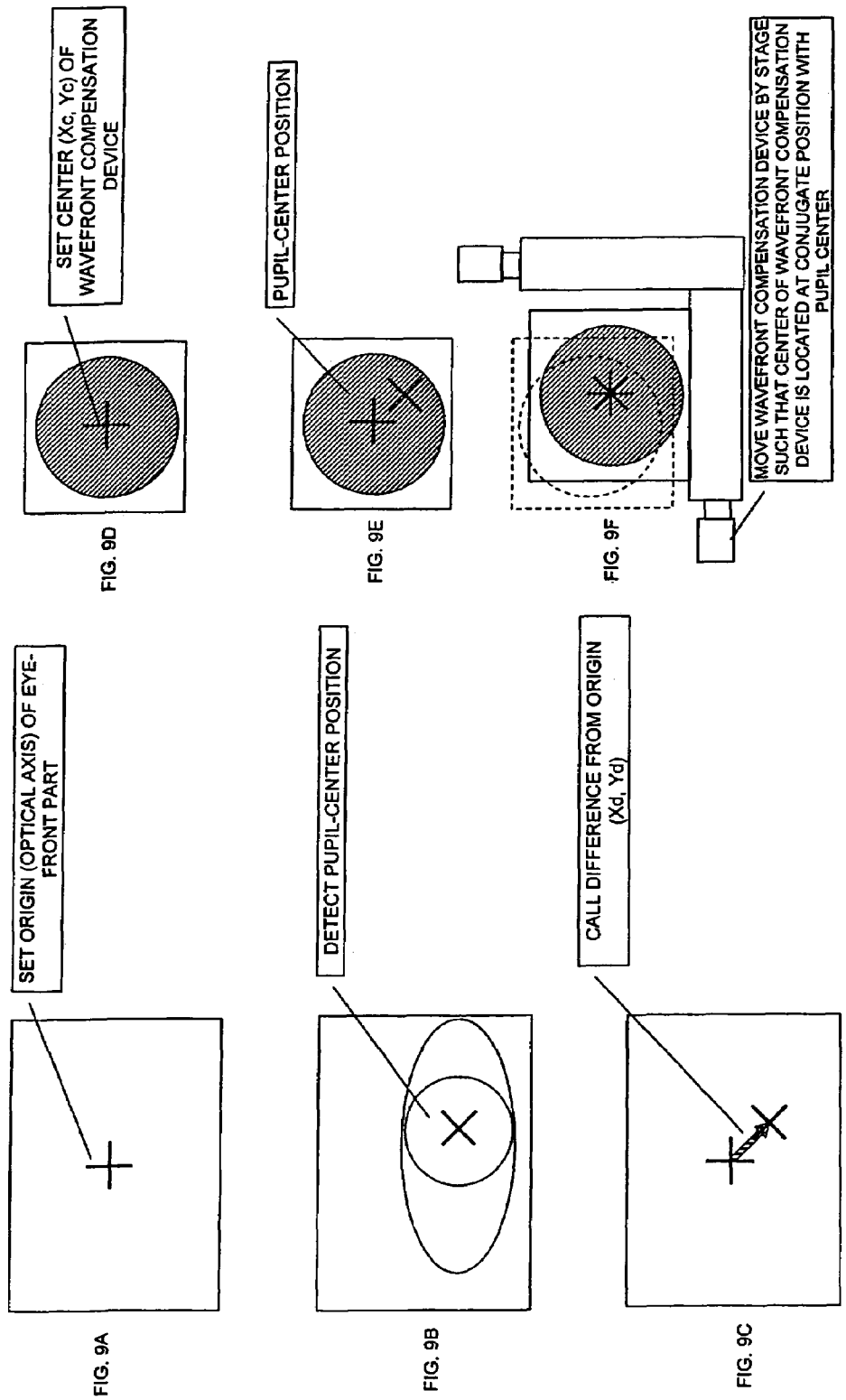
FIG. 9A to FIG. 9F are views showing the movement of the wavefront compensation device.

FIG. 8 is a flowchart of a compensation-device-movement adaptive optics in the present embodiment. FIG. 9 is a view showing the movement of the wavefront compensation device 71.

The computer 14 first specifies the origin of the eye-anterior-part image sensor 41 at a point thereof which is on the optical axis of the eye-anterior-part observation system in step S101. For example, the position of the optical axis of the eye-anterior-part observation system can be measured in advance by using a model eye. The computer 14 reads the origin point where the optical axis and the eye-anterior-part image sensor 41 intersect, measured in advance and stored in the memory 14-4, and uses it as the origin. For example, the origin of the eye-anterior-part image sensor 41 is specified as shown in FIG. 9A. The computer 14 turns on the eye-anterior-part illumination light source 45 in advance.

Next, the motor control circuit 16 drives the motor of the stage 73 with the motor to move the wavefront compensation device 71 and the stage 73 with the motor to make the center of the wavefront compensation device 71 on the optical axis in step S103. For example, as shown in FIG. 9D, the wavefront compensation device 71 is moved such that the center of the wavefront compensation device 71 matches the optical axis (indicated by "+" in the figure). The calculation apparatus 14-1 specifies the center (Xc, Yc) of the wavefront compensation device 71.

Then, the computer 14 specifies the initial position of the wavefront compensation device 71 in step S105. For example, the movement coordinates Xmo and Ymo of the wavefront compensation device 71 are set to zero, that is, Xmo=0 and Ymo=0. The computer 14 also sets the deformation of each element in the wavefront compensation device 71 to an initial value (zero, for example), and specifies the threshold hmax of a shift "h" in step S107. The threshold hmax of the shift "h" can be about half the distance between the actuators of the elements constituting the wavefront compensation device 71, but may also be changed, if necessary, depending on the device used.

The computer 14 performs alignment for the eye in step S109. Another alignment light source may be used. In the present embodiment, for example, a light beam reflected from the eye anterior part is incident on the eye-anterior-part image sensor 41, and the operator moves the entire apparatus or the eye is moved such that the center of the eye anterior part matches the origin of the eye-anterior-part image sensor 41 to implement alignment for the eye. The alignment for the eye may be performed at an appropriate timing.

Next, the pupil-movement-distance calculation section 14-2 executes pupil-movement-distance calculation processing in step S111. For example, the pupil-movement-distance calculation section 14-2 detects a shift (displacement of the eye under measurement, such as a shift Xd in the X direction and a shift Yd in the Y direction) of the center of the pupil from the optical axis, based on data sent from the eye-anterior-part image sensor (a CCD, for example) of the eye-anterior-part observation system, as shown in FIG. 9B and FIG. 9C. The pupil-movement-distance calculation section 14-2 also obtains a movement-position compensation shift "h", based on the detected shift. Details of the pupil-movement-distance calculation processing will be described later.

The pupil-movement-distance calculation section 14-2 determines in step S113 whether the obtained movement-position compensation shift "h" is smaller than the specified threshold hmax (h<hmax). Instead of this determination, it may be determined whether the obtained movement-position compensation shift "h" falls in a range determined in advance. When it is determined in step S113 that the obtained movement-position compensation shift "h" is not smaller than the specified threshold hmax, the pupil-movement-distance calculation section 14-2 executes wavefront-compensation-device-71 movement processing in step S115. For example, the pupil-movement-distance calculation section 14-2 determines the movement coordinates (Xmo, Ymo) of the wavefront compensation device 71 disposed at a conjugate point with the pupil, and sends the coordinates to the motor control circuit 16.

The motor control circuit 16 receives the movement coordinates (Xmo, Ymo), and drives the stage 73 with the motor such that the movement coordinates match the coordinates of the center of the wavefront compensation device 71, and the processing returns to the process of step S111. When the center of the pupil is located as shown in FIG. 9E, the movement coordinates (Xmo, Ymo) are set to the coordinates of the position of the center of the pupil, and the wavefront compensation device 71 is moved as shown in FIG. 9F. The present embodiment have features in which the wavefront compensation device 71, which is a part of the compensation optical section 70, is moved, and the movement method is as described above. Details of the movement processing of the wavefront compensation device 71 will be described later.

When it is determined in step S113 that the obtained movement-position compensation shift "h" is smaller than the specified threshold hmax, the calculation apparatus 14-1 turns on the wavefront-measurement light source to make light emitted from the light source incident on the eye under measurement in step S117.

Then, the calculation apparatus 14-1 executes shift-computation wavefront-measurement processing in step S119. For example, the calculation apparatus 14-1 obtains optical characteristics such as the Zernike coefficients and ocular aberration R from an image sent from the wavefront image sensor. Details of the shift-computation wavefront-measurement processing will be described later.

The calculation apparatus 14-1 determines in step S121 whether the aberration is sufficiently low. For example, the calculation apparatus 14-1 determines whether the obtained ocular aberration is lower than a threshold determined in advance. When it is determined in step S121 that the aberration is not sufficiently low, the calculation apparatus 14-1 deforms the wavefront compensation device 71 by the wavefront-compensation-device control apparatus 15 in step S123. For example, the calculation apparatus 14-1 determines the compensation of the wavefront compensation device according to the obtained optical characteristics, and outputs the compensation to the wavefront-compensation-device control apparatus 15. The compensation can be determined so as to cancel the measured aberration. The compensation may be determined according to a change in wavefront aberration. The wavefront-compensation-device control apparatus 15 generates a control signal based on the compensation sent from the calculation apparatus 14-1, and drives the actuator of each element constituting the wavefront compensation device 71 to deform the wavefront compensation device 71.

When it is determined in step S121 that the aberration is sufficiently low, the calculation apparatus 14-1 turns off the wavefront-measurement light source in step S125. When the wavefront-incident light source is turned off before an fundus-image, described below, is obtained, noise light is blocked to reduce noise on the image. The eyeground-illumination light source may be off during the processes of steps S117 to S125. The process of step S125 may be omitted. In the present embodiment, instead of turning on and off the light source, an appropriate mechanism for blocking illumination light may be inserted into and removed from a position on the optical axis.

Next, the fundus-image generation section 14-3 turns on the eyeground-illumination light source to make light emitted from the light source incident on the eye under measurement 60 in step S127. The eyeground-illumination light source may be turned on in advance. In this case, the process of step S127 may be omitted. The eyeground generation section 14-3 obtains an image of the eyeground in step S129 from the eye-anterior-part image sensor 41, which receives light reflected from the eyeground of the eye under measurement.

The obtained image of the eyeground is displayed on the display section 14-5 in step S131. With the use of the loop in this flowchart, even during wavefront compensation, an image of the eyeground taken previously can be displayed. Therefore, a sharp image always being compensated can be provided for the measurer. The fundus-image generation section 14-3 saves (stores) the obtained image of the eyeground in the storage section in step S133.

The computer 14 determines in step S135 whether to terminate the processing. For example, the computer 14 can receive an instruction from the operator at an appropriate input section to determine whether to terminate the processing. When it is determined in step S135 that the processing is not terminated, the fundus-image generation section 14-3 turns off the eyeground-illumination light source in step S137, and the processing returns to the process of step S111. The process of step S137 may be omitted. When it is determined in step S135 that the processing is to be terminated, the computer 14 terminates the processing.

Pupil-Movement-Distance Calculation Processing

Figure 10:
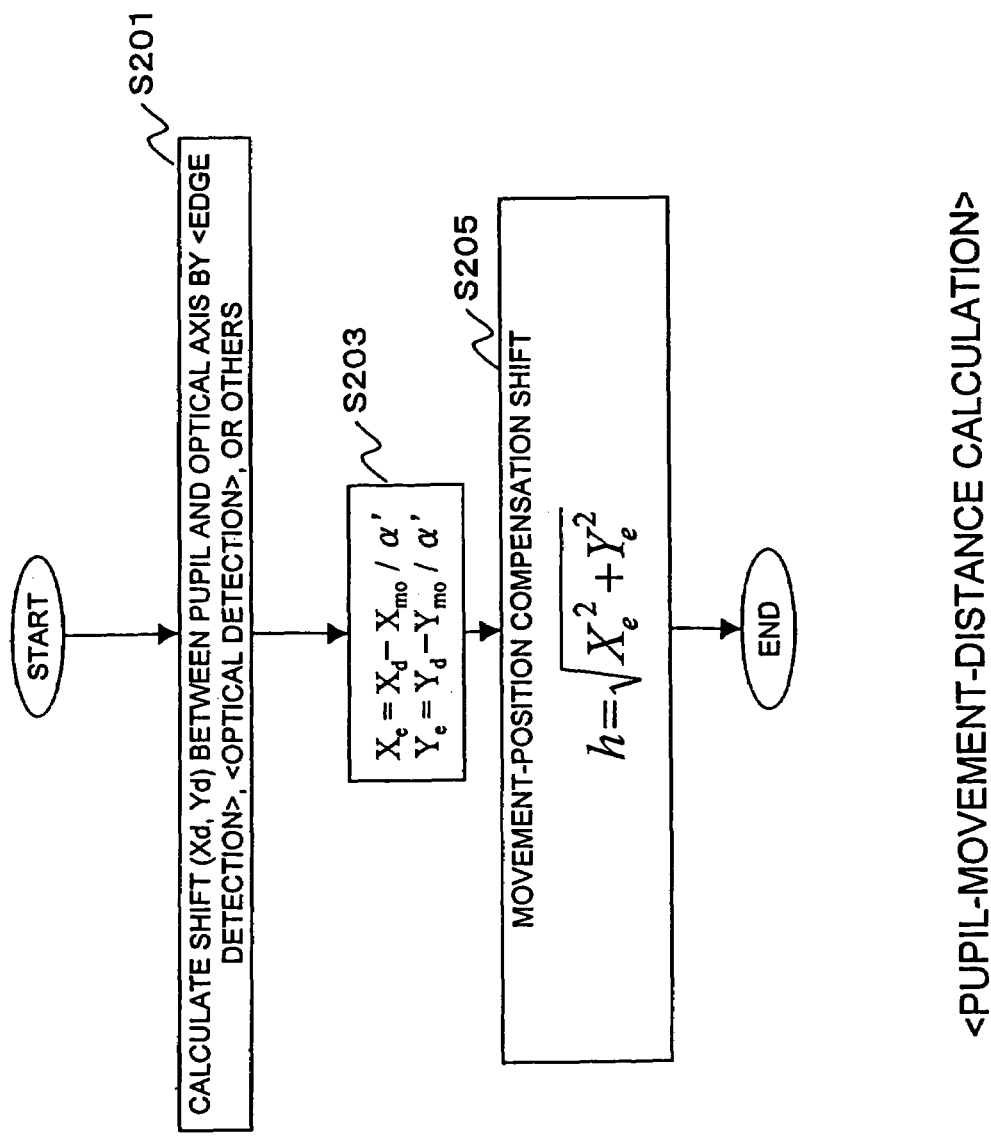
FIG. 10 is a detailed flowchart of pupil-movement-distance calculation processing.

FIG. 10 shows a detailed flowchart of pupil-movement-distance calculation processing. The pupil-movement-distance calculation section 14-2 first receives the eye-anterior-part image from the eye-anterior-part image sensor 41, and calculates a shift (Xd, Yd) between the pupil and the optical axis by edge detection, optical detection, or other methods in step S201.

Figure 11:
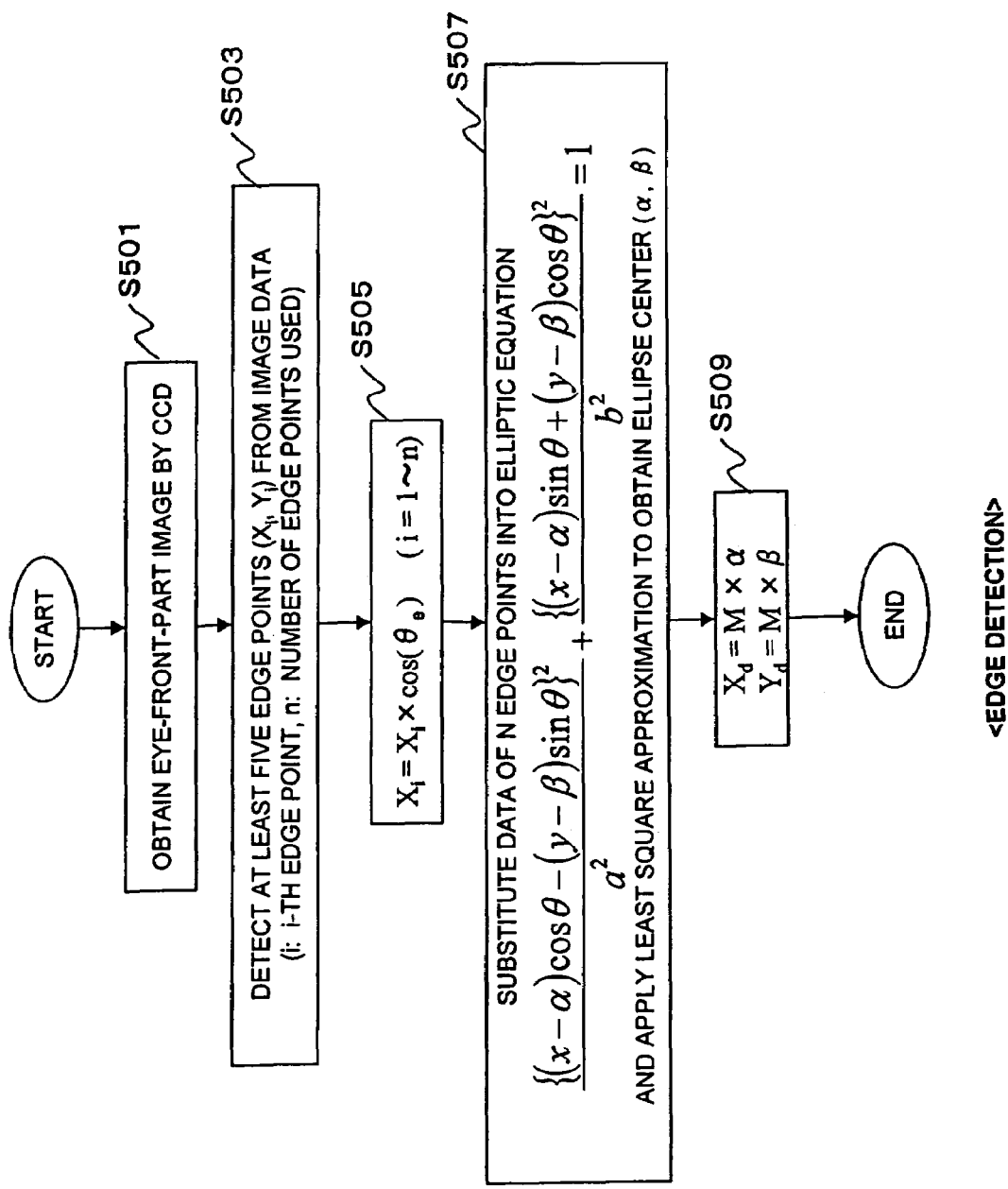
FIG. 11 is a detailed flowchart of edge detection.
Figure 12C:
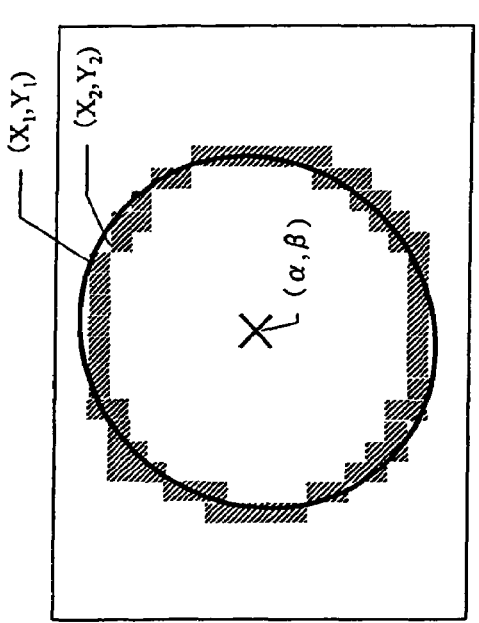
FIG. 12A to FIG. 12C are views showing the edge detection.
Figure 12A:
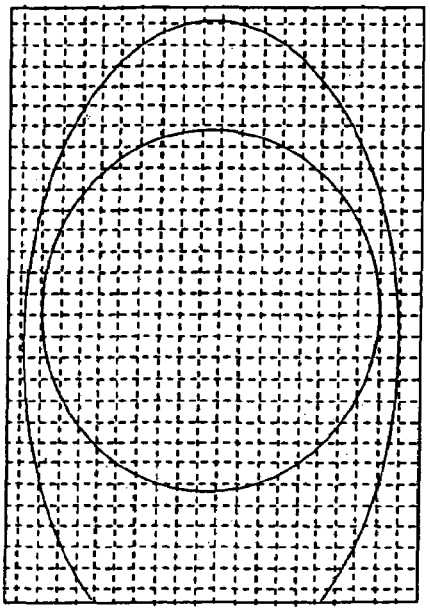
Figure 12B:
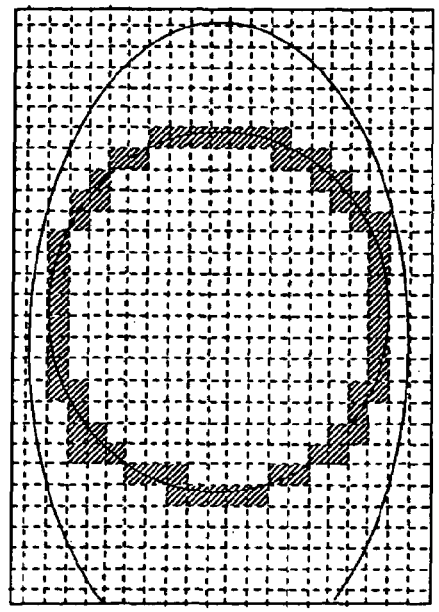

FIG. 11 is a detailed flowchart of edge detection. FIG. 12A to FIG. 12C are views showing an outline of the edge detection. The edge detection is taken here as an example method to calculate the shift (Xd, Yd) between the pupil and the optical axis. The optical detection will be described, later.

The pupil-movement-distance calculation section 14-2 obtains the eye-anterior-part image from the eye-anterior-part image sensor 41, such as a CCD, in step S501. FIG. 12A shows an outline of the obtained eye-anterior-part image. In FIG. 12A, an inner ellipse indicates the pupil.

Then, the pupil-movement-distance calculation section 14-2 detects at least five edge points (Xi, Yi) from the data of the eye-anterior-part image in step S503. For example, the pupil-movement-distance calculation section 14-2 can use an image processing method to detect changes (light and shade on the image) in the quantity of light of the obtained eye-anterior-part image and to obtain points on the edge of the pupil. Xi and Yi indicate the coordinates of the i-th edge point, where "i" is an appropriate identifier, and is, for example, 1 to n, and n indicates the number of detected edge points. The number of edge points to be detected may be determined in advance, or may fall in a range specified by a minimum value and/or a maximum value determined in advance. FIG. 12B shows an example edge detected. If the predetermined number of edge points is not obtained, the processing may be returned to step S501 so that the pupil-movement-distance calculation section 14-2 obtains another eye-anterior-part image to detect edge points.

Next, the pupil-movement-distance calculation section 14-2 coverts the x coordinate (Xi) of each detected edge point by the following expression in step S505.

$Xi=Xi\times\cos(\theta c)$ ($i$=1 to $n$)

where, θc indicates the angle formed between the eye-anterior-part image sensor 41 and the optical axis. When the eye-anterior-part image sensor 41 is provided at an angle with respect to the X axis as described above, the effect of the tilt on the X coordinate is removed by the above expression.

The pupil-movement-distance calculation section 14-2 substitutes the data (Xi, Yi) of the n edge points detected and converted, into the following elliptic equation for (x, y) to obtain the center coordinates (α, β) of the ellipse by, for example, the least square approximation in step S507. where, θ indicates the elliptic angle of the ellipse, and "a"

$$\frac{\{(x-\alpha)\cos\theta-(y-\beta)\sin\theta\}^2}{a^2}+\frac{\{(x-\alpha)\sin\theta+(y-\beta)\cos\theta\}^2}{b^2}=1$$

and "b" are constants. An appropriate method can be used to obtain "a" and "b", instead of the least square approximation. FIG. 12C shows the obtained center of the ellipse.

Then, the pupil-movement-distance calculation section 14-2 obtains the shift (Xd, Yd) between the pupil and the optical axis, based on the center (α, β) of the obtained ellipse, in step S509. For example, the pupil-movement-distance calculation section 14-2 obtains the shift (Xd, Yd) between the pupil and the optical axis according to the following expression.

$Xd=M\times\alpha$ $Yd=M\times\beta$ where, M indicates the magnification between the pupil and the eye-anterior-part image sensor, and can be stored in the memory 14-4 in advance. The pupil-movement-distance calculation section 14-2 completes the edge detection and, the processing returns, for example, to step S203.

Back to FIG. 10, the pupil-movement-distance calculation section 14-2 calculates (Xe, Ye) according to the following expression in step S203 based on the obtained shift (Xd, Yd) between the pupil and the optical axis.

$Xe=Xd-Xmo/\alpha'$ $Ye=Yd-Ymo/\alpha'$ where, α' indicates the magnification between the pupil and the wavefront compensation device 71, and can be stored in the memory 14-4 in advance. (Xe, Ye) corresponds to the shift between the center position of the pupil and the center of the wavefront compensation device 71, with the distance (Xmo, Ymo) subtracted by which the wavefront compensation device 71 has already moved.

The pupil-movement-distance calculation section 14-2 obtains the movement-position compensation shift "h" according to the following expression in step S205.

$h=\sqrt{X_e^2+Y_e^2}$

Wavefront-Compensation-Device Movement Processing

Figure 13:
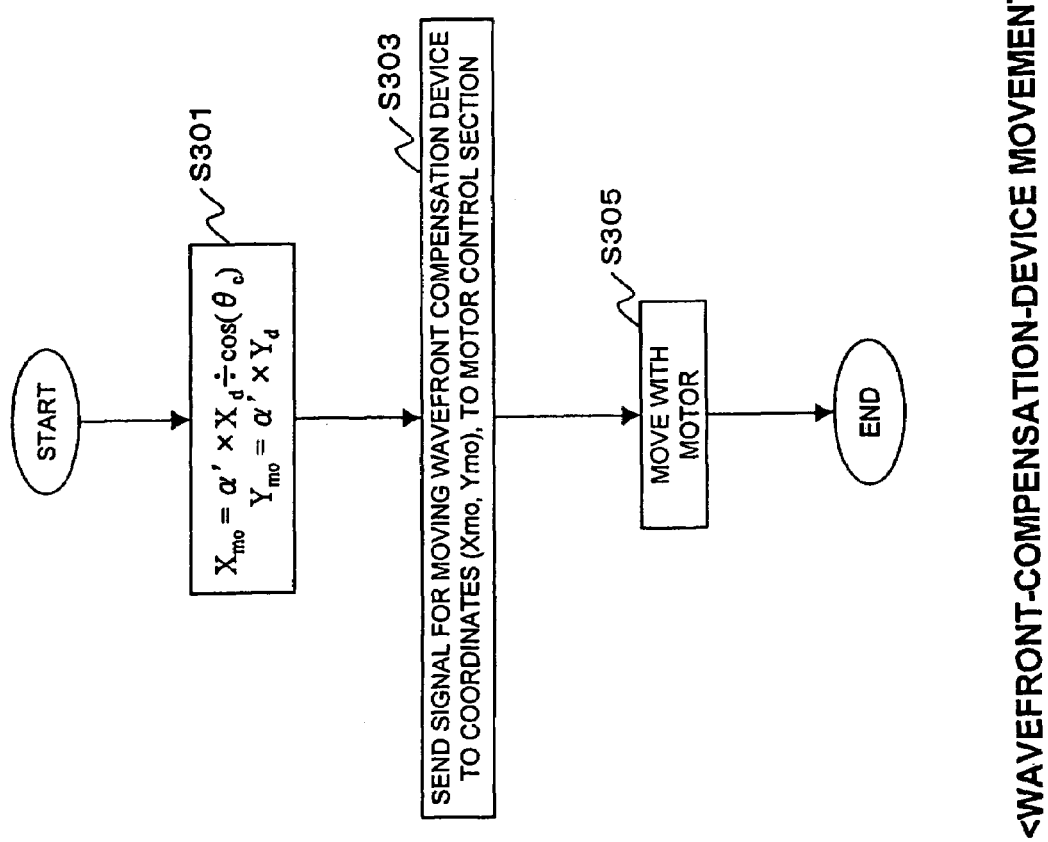
FIG. 13 is a detailed flowchart of wavefront-compensation-device movement processing.

FIG. 13 is a detailed flowchart of the wavefront-compensation-device-71 movement processing.

The pupil-movement-distance calculation section 14-2 first obtains the movement coordinates (Xmo, Ymo) of the wavefront compensation device 71 according to the following expressions in step S301.

$Xmo=\alpha'\times Xd \div \cos(\theta c)$ $Ymo=\alpha'\times Yd$ where, θc indicates the angle formed between the normal line of the wavefront compensation device 71 and the optical axis, and can be stored in the memory 14-4 in advance.

Next, the pupil-movement-distance calculation section 14-2 sends a signal used for moving the wavefront compensation device 71 to the obtained coordinates (Xmo, Ymo) to the motor control circuit 16 in step S303.

The motor control circuit 16 receives the signal from the pupil-movement-distance calculation section 14-2, and drives the motor of the stage 73 with the motor according to the received signal to move the wavefront compensation device 71 such that, for example, the center of the wavefront compensation device 71 matches the coordinates (Xmo, Ymo), in step S305.

Shift-Computation Wavefront-Measurement Processing

Figure 14:
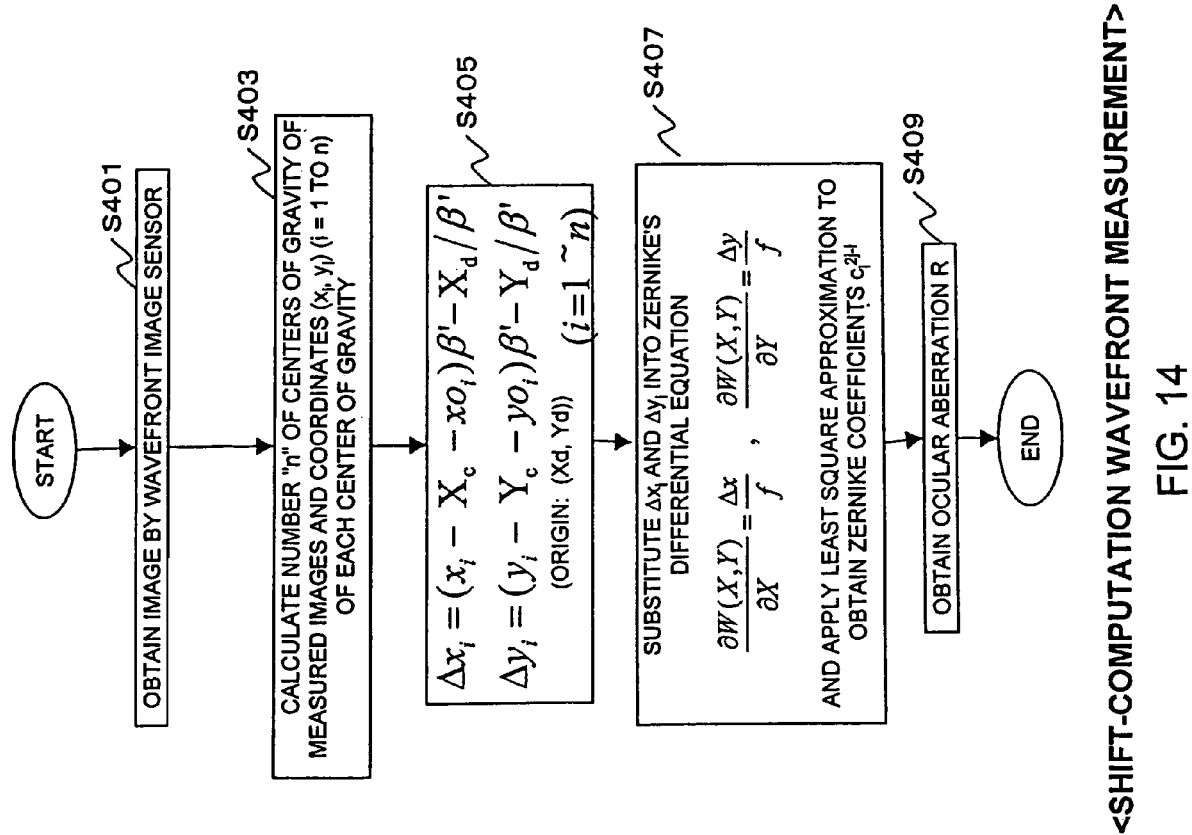
FIG. 14 is a detailed flowchart of shift-computation wavefront-measurement processing.

FIG. 14 is a detailed flowchart of the shift-computation wavefront-measurement processing.

The calculation apparatus 14-1 first obtains a measurement image from the wavefront image sensor in step S401. Then, the calculation apparatus 14-1 obtains the center of gravity of each point image in the measurement image and calculates the number "n" of the centers of gravity and their coordinates $(x_i, y_i)$ (i=1 to n) in step S403.

The calculation apparatus 14-1 obtains the movement distance $(\Delta x_i, \Delta y_i)$ of each point image according to the following expressions in step S405 based on the shift (Xd, Yd) between the pupil and the optical axis and the coordinates $(x_i, y_i)$ of the center of gravity of each point image.

$$\Delta x_i = (x_i - X_c - xo_i)\beta' - X_d/\beta'$$
$$\Delta y_i = (y_i - Y_c - yo_i)\beta' - Y_d/\beta'$$
$$(i = 1 \sim n)$$

where, $xo_i$ indicates the x coordinate of the i-th lens array of a division device, obtained at no aberration, $yo_i$ indicates the y coordinate of the i-th lens array of the division device, obtained at no aberration, Xc indicates the x coordinate of a point where the wavefront image sensor intersects with the optical axis, Yc indicates the y coordinate of the point where the wavefront image sensor intersects with the optical axis, and β' indicates the magnification between the wavefront image sensor and the pupil.

If the center of the pupil is shifted (the eye under measurement is shifted), the point where the light reflected from the point corresponding to the center of the pupil intersects with the wavefront image sensor 13 is also shifted. The coordinate origin of the wavefront image sensor 13, which receives light reflected from the eyeground of the eye under measurement, is specified as the center of the pupil. In the above expressions, items Xd/β' and Yd/β' correspond thereto. Instead of the center of the pupil, an appropriate position of the eye under measurement, such as the vertex of the cornea, can be used.

The calculation apparatus 14-1 substitutes the obtained $\Delta x_i$ and $\Delta y_i$ into the Zernike differential expressions and uses the least square approximation to obtain the Zernike coefficients $c_i^{2j-i}$ in step S407. The Zernike differential expressions are shown below.

$$\frac{\partial W(X,Y)}{\partial X} = \frac{\Delta x}{f}, \frac{\partial W(X,Y)}{\partial Y} = \frac{\Delta y}{f}$$

The calculation apparatus 14-1 obtains the quantity of ocular aberration R in step S409. For example, the quantity of ocular aberration $R_i^{2j-i}$ can be obtained by the following expression.

$$R_i^{2j-i} = \frac{\varepsilon_i^{2j-i}}{2(i+1)}(c_i^{2j-i})^2$$

-continued
$$(\varepsilon_i^{2j-i} = 2(2j = i), \varepsilon_i^{2j-i} = 1(2j \neq i))$$

The calculation apparatus 14-1 may further obtain optical characteristics of the eye under measurement 60, based on the obtained Zernike coefficients, the quantity of ocular aberration, and the compensation of the wavefront compensation device 71. As the compensation of the wavefront compensation device 71, the compensation output from the calculation apparatus 14-1 to the wavefront-compensation-device control apparatus 15, or the compensation corresponding to the control signal output from the wavefront-compensation-device control apparatus 15 to the wavefront compensation device 71 can be used. Alternatively, the compensation of the wavefront compensation device 71 is optically measured and used.

4. Optical Detection of Shift between Pupil and Optical Axis

FIG. 15 is a view showing an eyeground observation apparatus which optically detects the pupil. As described in step S201, the shift between the pupil and the optical axis can be optically detected, instead of using the edge detection.

The eyeground observation apparatus includes a wavefront compensation system 1, an eyeground illumination system 2, an eyeground observation system 3, an eye-anterior-part observation system 4, an eye-anterior-part illumination light source 45, a fixation system 5, a compensation optical section 70, a motor control circuit 16, a pupil-movement-distance calculation section 14-2, and an fundus-image generation section 14-3. The eyeground observation apparatus further includes limbus-detection light sources 91, limbus-detection light-receiving sections 92, and a limbus-detection-signal calculation section 14-6. The same symbols as those used in FIG. 1 are assigned to the same components as those shown in FIG. 1, and a detailed description thereof will be omitted.

The limbus-detection light sources 91 irradiate light around the pupil ring portion (or limbus) of the eye under measurement. For example, a plurality of limbus-detection light sources 91 is provided to irradiate light at a position determined in advance of the eye under measurement 60. LEDs having a wavelength of 940 nm can be used as the limbus-detection light sources 91. The limbus-detection light sources 91 are not limited to the LEDs. Any appropriate light sources may be used.

The limbus-detection light-receiving sections 92 receive light reflected around the pupil of the eye under measurement 60 when light emitted from the limbus-detection light sources 91 illuminate the eye under measurement 60. For example, a plurality of limbus-detection light-receiving sections 92 is provided corresponding to the limbus-detection light sources 91. For example, photodiodes can be used as the limbus-detection light-receiving sections 92. The limbus-detection light-receiving sections 92 are not limited to the photodiodes. Any appropriate light-receiving devices or sections may be used. At least two limbus-detection light sources 91 and two limbus-detection light-receiving sections 92 are required, but it is preferred that four limbus-detection light sources 91 and light-receiving sections 92 be used. The limbus-detection-signal calculation section 14-6 receives light-receiving signals from the limbus-detection light-receiving sections 92 and obtains the quantity of light based on the light-receiving signals. The limbus-detection-signal calculation section 14-6 also calculates the shift of the pupil.

FIG. 16A to FIG. 16E show an outline of optical pupil detection. These figures show a case in which four limbus-detection light sources 91 and four limbus-detection light-receiving sections 92 are provided. The limbus-detection light sources 91 illuminate the ring portion of the pupil, as shown in FIG. 16A.

Assuming that a limbus-detection light-receiving section 92 receives the quantity $W_1$ of light when the pupil has no shift as shown in FIG. 16C, when the pupil shifts toward the optical axis (upper direction in the figure) of the limbus-detection light source 91 as shown in FIG. 16D, the limbus-detection light-receiving section 92 receives the quantity W of light which is smaller than $W_1$ ($W<W_1$). On the other hand, as shown in FIG. 16E, when the pupil shifts away from the optical axis (toward the lower direction in the figure) of the limbus-detection light source 91, the limbus-detection light-receiving section 92 receives the quantity W of light which is larger than $W_1$ ($W>W_1$).

Since the quantity of light detected by the limbus-detection light-receiving section 92 changes in this way as the pupil shifts, the center of the pupil and/or the shift of the pupil can be obtained based on the quantity of light detected, if limbus-detection light sources 91 and limbus-detection light-receiving sections 92 are appropriately provided.

FIG. 16B shows a case in which the pupil has shifted from a dotted-line position to a solid-line position. When the pupil shifts, the quantity of light detected by limbus-detection light-receiving sections 92 is changed. Among four limbus-detection light-receiving sections 92 shown in FIG. 16B, the left and lower limbus-detection light-receiving sections 92 detect a larger quantity of light whereas the right and upper limbus-detection light-receiving sections 92 detect a smaller quantity of light.

When the pupil shifts in the right direction in FIG. 16B, for example, since the zone where the right illuminated area and the pupil overlap increases, the quantity of light detected by a limbus-detection light-receiving section 92 which receives light reflected from the right illuminated area becomes smaller. Since the zone where the left illuminated area and the pupil overlap decreases, the quantity of light detected by a limbus-detection light-receiving section 92 which receives light reflected from the left illuminated area becomes larger. The same situations are applied to light receiving at the upper and lower illuminated areas.

FIG. 17 is a flowchart of the optical pupil detection, which is a detailed flowchart of the process of step S201, described above.

The limbus-detection-signal calculation section 14-6 specifies initial settings in step S601. For example, the limbus-detection-signal calculation section 14-6 sets a parameter "i" to "1" and the sum of the quantity of light $W_{ALL}$ to zero. Then, the limbus-detection-signal calculation section 14-6 turns on the i-th limbus-detection light source 91 to make light incident on the eye under measurement in step S603. If other limbus-detection light sources are on, the limbus-detection-signal calculation section 14-6 may turn them off.

The limbus-detection-signal calculation section 14-6 also obtains the eye-anterior-part position $(x_i, y_i)$ where light is incident, in step S605. For example, the eye anterior-position $(x_i, y_i)$ where light is incident is stored in the memory 14-4 in advance correspondingly to each limbus-detection light source 91, and the limbus-detection-signal calculation section 14-6 refers to the memory 14-4 to obtain the eye anterior-position $(x_i, y_i)$ where light is incident corresponding to the limbus-detection light source turned on. The limbus-detection-signal calculation section 14-6 may store the obtained eye-anterior-part position $(x_i, y_i)$ where light is incident, in the memory 14-4.

The limbus-detection-signal calculation section 14-6 measures the quantity of light $W_i$ received by the i-th limbus-detection light-receiving section, in step S607. For example, the limbus-detection-signal calculation section 14-6 receives a light-receiving signal from the limbus-detection light-receiving section 92 corresponding to the limbus-detection light source 91 turned on, and detects the quantity of light, based on the light-receiving signal.

The limbus-detection-signal calculation section 14-6 adds the detected quantity of light $W_i$ to the sum of the quantity of light $W_{ALL}$ in step S609.

$$W_{ALL} = W_{ALL} + W_i$$

The limbus-detection-signal calculation section 14-6 determines in step S611 whether the parameter "i" is smaller than the number "m" of pairs of the limbus-detection light sources 91 and the limbus-detection light-receiving sections 92 (i<m). The number "m" can be stored in the memory 14-4 in advance.

When it is determined in step S611 that the parameter "i" is smaller than the number "m", the limbus-detection-signal calculation section 14-6 increments the parameter "i", for example, by 1 in step S613, and repeats the processes of step S603 and subsequent steps. In the present flowchart, the processes of steps S603 to S611 related to the limbus-detection light source 91 and the limbus-detection light-receiving section 92 for the parameter "i" is sequentially executed in series. The process of each step may be performed for all limbus-detection light sources 91 and limbus-detection light-receiving sections 92.

When it is determined in step S611 that the parameter "i" is not smaller than the number "m", the limbus-detection-signal calculation section 14-6 obtains the shift between the pupil and the optical axis in step S615 based on the eye-anterior-part position $(x_i, y_i)$ where light is incident, the measured quantity of light $W_i$, and the sum of the quantity of light $W_{ALL}$. For example, the limbus-detection-signal calculation section 14-6 obtains the shift (Xd, Yd) between the pupil and the optical axis by the following expressions.

$$X_d = \frac{1}{W_{ALL}} \sum_{i=1}^{m} \gamma_i W_i x_i$$

$$Y_d = \frac{1}{W_{ALL}} \sum_{i=1}^{m} \gamma_i W_i y_i$$

where, γi indicates a compensation value depending on the measurement conditions and the limbus-detection light-receiving sections 92, and can be stored in the memory 14-4 in advance. In the same way as in the expressions to obtain the center of gravity, the weight of the quantity of light is applied to calculate the center. The limbus-detection-signal calculation section 14-6 completes the optical pupil detection processing, and returns, for example, to the process of step S203.

5. Display Examples

Figure 18:
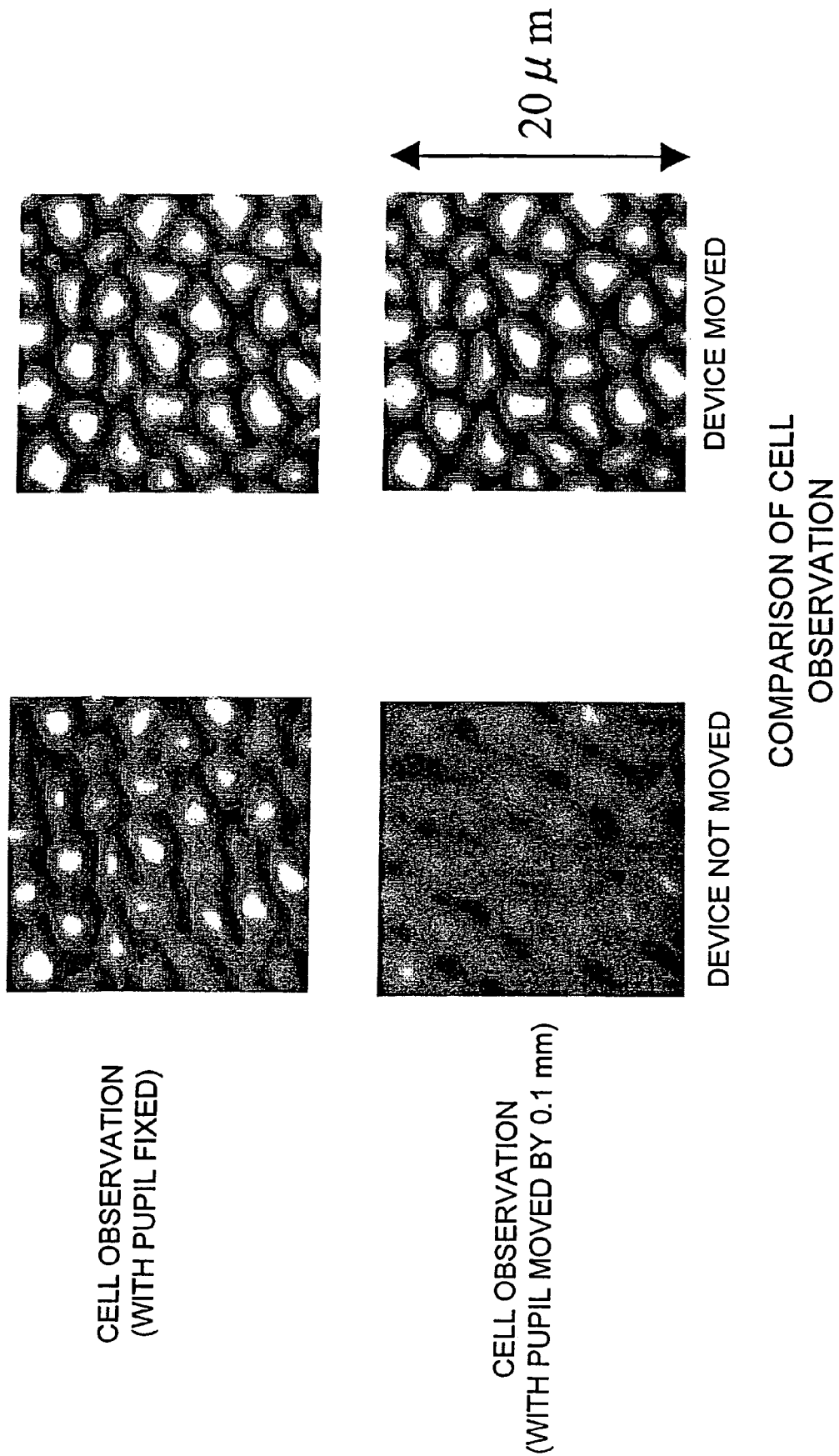
FIG. 18 is a view showing display examples of fundus-images.

FIG. 18 shows display examples of fundus-images (cell observation). In FIG. 18, fundus-images obtained when the wavefront compensation device 71 is not moved are shown at the left-hand side, whereas fundus-images obtained when the wavefront compensation device 71 is moved in the present embodiment are shown at the right-hand side. In the figure, fundus-images obtained when the center of the pupil is fixed on the optical axis are shown at the upper side, whereas fundus-images obtained when the center of the pupil is moved by 0.1 mm away from the optical axis are shown at the lower side. When the wavefront compensation device 71 is not moved, if the pupil moves, fundus-images become blurred. When the wavefront compensation device 71 is moved as in the present embodiment, even if the pupil moves, clear fundus-images are obtained.

Fundus-images may be images from which the entire eyeground or a predetermined area can be observed, instead of those shown in FIG. 18 where cells can be observed. In addition, fundus-images may be images enlarged or contracted, compared with those shown in FIG. 18, images having different resolutions from that of the images shown in FIG. 18, or images having different magnifications from that of the images shown in FIG. 18.

This application claims priority from Japanese Patent Application 2004-183389, filed Jun. 22, 2004, which is incorporated herein by reference in its entirety.

What is claimed is:

1. An optical-characteristic measurement apparatus comprising:
    an eye-anterior-part illumination light source for illuminating an eye anterior part of an eye under measurement;
    an eye-anterior-part observation section for receiving light reflected from the eye anterior part of the eye under measurement illuminated, and for generating an eye anterior image of the eye under measurement;
    a movement-distance calculation section for measuring the displacement of the eye under measurement indicating the shift between an optical axis and the eye under measurement, based on the generated eye anterior image;
    a wavefront compensation device for compensating the wavefront of light reflected or transmitted, based on a given control signal;
    a wavefront measurement section for projecting light used for wavefront measurement on the eyeground of the eye under measurement and for receiving light reflected from the eyeground of the eye under measurement through the wavefront compensation device;
    an aberration calculation section for measuring wavefront aberration of the eye under measurement, based on the displacement of the eye under measurement measured by the movement-distance calculation section and a light-receiving signal obtained by the wavefront measurement section;
    a stage for moving the wavefront compensation device, based on the displacement of the eye under measurement measured by the movement-distance calculation section, in a direction transversing the optical axis of the light reflected from the eyeground of the eye under measurement or in a direction of a plane perpendicular to a normal line of the wavefront compensation device; and
    a wavefront-compensation-device control apparatus for generating a control signal used to perform wavefront compensation such that aberration becomes small, based on the wavefront aberration measured by the aberration calculation section, and for outputting the generated control signal to the wavefront compensation device to compensate the wavefront,
    wherein the aberration calculation section measures an optical characteristic of the eye under measurement, based on the compensation of the wavefront compensation device corresponding to the control signal for the wavefront compensation, the displacement of the eye under measurement measured by the movement-distance calculation section, and the light-receiving signal obtained by the wavefront measurement section after the wavefront is compensated by the wavefront compensation device.

2. An optical-characteristic measurement apparatus according to claim 1, wherein
    the stage is moved such that the displacement of the eye under measurement measured by the movement-distance calculation section falls in a predetermined range, and
    the wavefront-compensation-device control apparatus is configured to output the control signal used by the wavefront compensation device to perform wavefront compensation, based on the wavefront aberration measured by the aberration calculation section, after the stage is moved.

3. An optical-characteristic measurement apparatus according to claim 1, wherein the wavefront measurement section comprises:
    a point-image-projection optical system for projecting light for wavefront measurement to the eyeground of the eye under measurement, the point-image-projection optical system comprising a wavefront-measurement light source;
    a light-receiving optical system for receiving the light reflected from the eyeground of the eye under measurement, the light-receiving optical system comprising a division device for dividing the light reflected from the eyeground of the eye under measurement through the wavefront compensation device into a plurality of light beams, and the wavefront compensation device being disposed in the light-receiving optical system; and
    a wavefront image sensor for receiving light reflected from the eyeground of the eye under measurement through the wavefront compensation device and the division device.

4. An optical-characteristic measurement apparatus according to claim 1, wherein
    the aberration calculation section specifies the coordinate origin of a wavefront image sensor for receiving light reflected from the eyeground of the eye under measurement, at the center of the pupil or the vertex of the cornea, based on the displacement of the eye under measurement measured by the movement-distance calculation section; and
    the wavefront-compensation-device control apparatus is configured to generate the control signal used by the wavefront compensation device to perform wavefront compensation, based on wavefront aberration or a change in wavefront aberration in a coordinate system of which the coordinate origin is specified by the aberration calculation section.

5. An optical-characteristic measurement apparatus according to claim 1, wherein
    the wavefront compensation device is provided such that its normal-line direction is titled at a predetermined angle with respect to the optical axis of the light reflected from the eyeground of the eye under measurement;
    the eye-anterior-part observation section comprises an eye-anterior-part image sensor for receiving the light reflected from the eye anterior part of the eye under measurement illuminated; and the eye-anterior-part image sensor is provided at a tilt angle with respect to the optical axis of the light reflected from the eye anterior part of the eye under measurement, the tilt angle being the same or almost the same as the predetermined angle formed by the optical axis and the normal-line direction of the wavefront compensation device.

6. An optical-characteristic measurement apparatus according to claim 1, wherein the eye-anterior-part observation section comprises an eye-anterior-part image sensor disposed at a predetermined tilt angle with respect to the optical axis of the light reflected from the eye anterior part of the eye under measurement, for receiving the light reflected from the eye anterior part of the eye under measurement illuminated to generate the eye anterior image; and
   the movement-distance calculation section obtains the eye anterior image from the eye-anterior-part image sensor,
   detects a plurality of edge of the pupil from the obtained eye anterior image and obtains the coordinates of each edge point,
   compensates the obtained coordinates of each edge point for the tilt of the eye-anterior-part image sensor according to the obtained coordinates of each edge point and the tilt angle of the eye-anterior-part image sensor,
   obtains the center of an ellipse or a circle according to the compensated coordinates of each edge point, and
   obtains the displacement of the eye under measurement indicating the shift between the pupil and the optical axis by multiplying the obtained center of the ellipse or the circle by a magnification determined in advance between the pupil and the eye-anterior-part image sensor.

7. An optical-characteristic measurement apparatus according to claim 1, further comprising:
   a plurality of limbus-detection light sources for illuminating a predetermined area around a pupil ring portion of the eye under measurement with light;
   a plurality of limbus-detection light-receiving sections corresponding to the plurality of limbus-detection light sources, for receiving reflected light which is emitted from the plurality of limbus-detection light sources and reflected around the pupil of the eye under measurement; and
   a limbus-detection-signal calculation section for obtaining a shift between the pupil and an optical axis, based on light-receiving signals of the plurality of limbus-detection light-receiving sections,
   wherein the limbus-detection-signal calculation section
   measures the quantity of the light received by each of the plurality of limbus-detection light-receiving sections, based on the light-receiving signal of the each of the plurality of limbus-detection light-receiving sections,
   obtains the sum of each of the measured quantity of the light, and
   obtains the displacement of the eye under measurement, based on a exe-front-part position where light emitted from each of the plurality of limbus-detection light sources is incident, each of the measured quantity of the light, and the sum of each of the measured quantity of the light.

8. An optical-characteristic measurement apparatus according to claim 7, wherein the limbus-detection-signal calculation section obtains the displacement Xd and Yd of the eye under measurement according to the following expressions, based on the eye-anterior-part position $(x_i, y_i)$ where light emitted from each of the limbus-detection light sources is incident, each of the measured quantity of the light $W_i$, and the sum of each of the measured quantity of the light $W_{ALL}$ $$X_d = \frac{1}{W_{ALL}} \sum_{i=1}^{m} \gamma_i W_i x_i$$

$$Y_d = \frac{1}{W_{ALL}} \sum_{i=1}^{m} \gamma_i W_i y_i$$

where, γi indicates a compensation value determined in advance according to the plurality of limbus-detection light-receiving sections and/or measurement conditions, and m indicates the number of the plurality of limbus-detection light-receiving sections or the number of the plurality of limbus-detection light sources.

9. An optical-characteristic measurement apparatus according to claim 1, wherein the aberration calculation section obtains the coordinates $(x_i, y_i)$ (i is an integer ranging from 1 to n) of the center of gravity of each of point images of a predetermined number "n" from the light-receiving signal obtained by the wavefront measurement section,
   obtains a shift $(\Delta x_i, \Delta y_i)$ of each point image according to the following expressions, based on the obtained coordinates $(x_i, y_i)$ of the center of gravity, and the measured displacement (Xd, Yd) of the eye under measurement, and
   obtains an optical characteristic of the eye under measurement, based on the obtained shift $(\Delta x_i, \Delta y_i)$ of each point image, $$\Delta x_i = (x_i - X_c - xo_i)\beta' - X_d/\beta'$$
$$\Delta y_i = (y_i - Y_c - yo_i)\beta' - Y_d/\beta'$$
$$(i = 1 \sim n)$$

where, $xo_i$ indicates the x coordinate of the i-th lens array of a division device, at no aberration, $yo_i$ indicates the y coordinate of the i-th lens array of the division device, at no aberration, Xc indicates the x coordinate of a point where a wavefront image sensor intersects with the optical axis, Yc indicates the y coordinate of the point where the wavefront image sensor intersects with the optical axis, and β' indicates a magnification between the wavefront image sensor and the pupil.

10. An fundus-image observation apparatus comprising:
   an eye-anterior-part illumination light source for illuminating an eye anterior part of an eye under measurement;
   an eye-anterior-part observation section for receiving light reflected from the eye anterior part of the eye under measurement illuminated, and for generating an eye anterior image of the eye under measurement;
   a movement-distance calculation section for measuring the displacement of the eye under measurement indicating the shift between an optical axis and the eye under measurement, based on the generated eye anterior image;
   a wavefront compensation device for compensating the wavefront of light reflected or transmitted, based on a given control signal;
   a wavefront measurement section for projecting light used for wavefront measurement on the eyeground of the eye under measurement and for receiving first light reflected from the eyeground of the eye under measurement illuminated by the light used for wavefront measurement, through the wavefront compensation device;

an aberration calculation section for measuring wavefront aberration of the eye under measurement, based on the displacement of the eye under measurement measured by the movement-distance calculation section and a light-receiving signal obtained by the wavefront measurement section;

an eyeground illumination system for illuminating a predetermined area on the eyeground of the eye under measurement with light for eyeground observation;

an eyeground observation system for receiving second light reflected from the eyeground of the eye under measurement illuminated by the light emitted by the eyeground illumination system, through the wavefront compensation device, and for generating an fundus-image;

an fundus-image generation section for obtaining the fundus-image generated by the eyeground observation system and for displaying or outputting the fundus-image;

a stage for moving the wavefront compensation device, based on the displacement of the eye under measurement measured by the movement-distance calculation section, in a direction transversing the optical axis of the first and/or second light reflected from the eyeground of the eye under measurement or in a direction of a plane perpendicular to a normal line of the wavefront compensation device; and a wavefront-compensation-device control apparatus for generating a control signal used to perform wavefront compensation such that aberration becomes small, based on the wavefront aberration measured by the aberration calculation section, and for outputting the generated control signal to the wavefront compensation device to compensate the wavefront, wherein the fundus-image generation section obtains an fundus-image which is after the stage is moved and compensated by the wavefront compensation device.

11. An fundus-image observation apparatus according to claim 10, wherein the stage is moved such that the displacement of the eye under measurement measured by the movement-distance calculation section falls in a predetermined range, and the wavefront-compensation-device control apparatus is configured to output the control signal used by the wavefront compensation device to perform wavefront compensation, based on the wavefront aberration measured by the aberration calculation section, after the stage is moved.

12. An fundus-image observation apparatus according to claim 10, wherein the wavefront measurement section comprises:

a point-image-projection optical system for projecting light for wavefront measurement to the eyeground of the eye under measurement, the point-image-projection optical system comprising a wavefront-measurement light source;

a light-receiving optical system for receiving the first light reflected from the eyeground of the eye under measurement projected the light, the light-receiving optical system comprising a division device for dividing the first light reflected from the eyeground of the eye under measurement through the wavefront compensation device into a plurality of light beams, and the wavefront compensation device being disposed in the light-receiving optical system; and a wavefront image sensor for receiving the first light reflected from the eyeground of the eye under measurement through the wavefront compensation device and the division device.

13. An fundus-image observation apparatus according to claim 10, wherein the aberration calculation section specifies the coordinate origin of a wavefront image sensor for receiving the first light reflected from the eyeground of the eye under measurement, at the center of the pupil or the vertex of the cornea, based on the displacement of the eye under measurement measured by the movement-distance calculation section; and the wavefront-compensation-device control apparatus is configured to generate the control signal used by the wavefront compensation device to perform wavefront compensation, based on wavefront aberration or a change in wavefront aberration in a coordinate system of which the coordinate origin is specified by the aberration calculation section.

14. An fundus-image observation apparatus according to claim 10, wherein the wavefront compensation device is provided such that its normal-line direction is titled at a predetermined angle with respect to the optical axis of the first and second light reflected from the eyeground of the eye under measurement;

the eye-anterior-part observation section comprises an eye-anterior-part image sensor for receiving the light reflected from the eye anterior part of the eye under measurement illuminated; and the eye-anterior-part image sensor is provided at a tilt angle with respect to the optical axis of the light reflected from the eye anterior part of the eye under measurement, the tilt angle being the same or almost the same as the predetermined angle formed by the optical axis and the normal-line direction of the wavefront compensation device.

15. An fundus-image observation apparatus according to claim 10, wherein the eyeground observation system comprises a cornea-reflection removing mirror or a cornea-reflection removing pattern.

16. An fundus-image observation apparatus according to claim 10, wherein the eyeground observation system comprises:

an fundus-image sensor for receiving the second light reflected;

a wavelength plate for polarizing the second light reflected;

a mirror having an opening for removing noise sent from the cornea from the second light reflected; and a polarization beam splitter for guiding the second light reflected, modulated by the wavefront compensation device to the wavelength plate and to the mirror having the opening, and for guiding light polarized by the wavelength plate and reflected by and returned from the mirror having the opening to the fundus-image sensor.

17. An fundus-image observation apparatus according to claim 10, wherein the eye-anterior-part observation section comprises an eye-anterior-part image sensor disposed at a predetermined tilt angle with respect to the optical axis of the light reflected from the eye anterior part of the eye under measurement, for receiving the light reflected from the eye anterior part of the eye under measurement illuminated, to generate the eye anterior image; and the movement-distance calculation section obtains the eye anterior image from the eye-anterior-part image sensor, detects a plurality of edge of the pupil from the obtained eye anterior image and obtains the coordinates of each edge point, compensates the obtained coordinates of each edge point for the tilt of the eye-anterior-part image sensor according to the obtained coordinates of each edge point and the tilt angle of the eye-anterior-part image sensor, obtains the center of an ellipse or a circle according to the compensated coordinates of each edge point, and obtains the displacement of the eye under measurement indicating the shift between the pupil and the optical axis by multiplying the obtained center of the ellipse or the circle by a magnification determined in advance between the pupil and the eye-anterior-part image sensor.

18. An fundus-image observation apparatus according to claim 10, further comprising:

a plurality of limbus-detection light sources for illuminating a predetermined area around a pupil ring portion of the eye under measurement with light;

a plurality of limbus-detection light-receiving sections corresponding to the plurality of limbus-detection light sources, for receiving reflected light which is emitted from the plurality of limbus-detection light sources and reflected around the pupil of the eye under measurement; and a limbus-detection-signal calculation section for obtaining a shift between the pupil and an optical axis, based on light-receiving signals of the plurality of limbus-detection light-receiving sections, wherein the limbus-detection-signal calculation section measures the quantity of the light received by each of the plurality of limbus-detection light-receiving sections, based on the light-receiving signal of the each of the plurality of limbus-detection light-receiving sections, obtains the sum of each of the measured quantity of the light, and obtains the displacement of the eye under measurement, based on a eye-anterior-part position where light emitted from each of the plurality of limbus-detection light sources is incident, each of the measured quantity of the light, and the sum of each of the measured quantity of the light.

19. An fundus-image observation apparatus according to claim 18, wherein the limbus-detection-signal calculation section obtains the displacement Xd and Yd of the eye under measurement according to the following expressions, based on the eye-anterior-part position $(x_i, y_i)$ where light emitted from each of the plurality of limbus-detection light sources is incident, each of the measured quantity of the light $W_i$, and the sum of each of the measured quantity of the light $W_{ALL}$ $$X_d = \frac{1}{W_{ALL}} \sum_{i=1}^{m} \gamma_i W_i x_i$$

$$Y_d = \frac{1}{W_{ALL}} \sum_{i=1}^{m} \gamma_i W_i y_i$$

where, $\gamma i$ indicates a compensation value determined in advance according to the plurality of limbus-detection light-receiving sections and/or measurement conditions, and m indicates the number of the plurality of limbus-detection light-receiving sections or the number of the plurality of limbus-detection light sources.

20. An fundus-image observation apparatus according to claim 10, wherein the aberration calculation section obtains the coordinates $(x_i, y_i)$ (i is an integer ranging from 1 to n) of the center of gravity of each of a predetermined number "n" of point images from the light-receiving signal obtained by the wavefront measurement section, obtains a shift $(\Delta x_i, \Delta y_i)$ of each point image according to the following expressions, based on the obtained coordinates $(x_i, y_i)$ of the center of gravity, and the measured displacement (Xd, Yd) of the eye under measurement, and obtains an optical characteristic of the eye under measurement, based on the obtained shift $(\Delta x_i, \Delta y_i)$ of each point image, $$\Delta x_i = (x_i - X_c - xo_i)\beta' - X_d/\beta'$$
$$\Delta y_i = (y_i - Y_c - yo_i)\beta' - Y_d/\beta'$$
$$(i = 1 \sim n)$$

where, $xo_i$ indicates the x coordinate of an i-th lens array of a division device, at no aberration, $yo_i$ indicates the y coordinate of the i-th lens array of the division device, at no aberration, Xc indicates the x coordinate of a point where a wavefront image sensor intersects with the optical axis, Yc indicates the y coordinate of the point where the wavefront image sensor intersects with the optical axis, and $\beta'$ indicates a magnification between the wavefront image sensor and the pupil.

* * * * *